United States Patent
Hori et al.

(10) Patent No.: US 8,668,933 B2
(45) Date of Patent: Mar. 11, 2014

(54) POLYION COMPLEX OF DOUBLE-STRANDED RIBONUCLEIC ACID

(75) Inventors: Yuichi Hori, Tokyo (JP); Kazunori Kataoka, Tokyo (JP); Toshiro Fujita, Tokyo (JP); Hideki Shimizu, Tokyo (JP); Shinya Kaname, Tokyo (JP); Satoru Matsumoto, Tokyo (JP); Nobuhiro Nishiyama, Tokyo (JP); Kanjiro Miyata, Tokyo (JP); Makoto Oba, Tokyo (JP)

(73) Assignee: The University of Tokyo, Tokyo (JP)

( * ) Notice: Subject to any disclaimer, the term of this patent is extended or adjusted under 35 U.S.C. 154(b) by 54 days.

(21) Appl. No.: 13/259,961

(22) PCT Filed: Mar. 31, 2010

(86) PCT No.: PCT/JP2010/055826
§ 371 (c)(1),
(2), (4) Date: Dec. 7, 2011

(87) PCT Pub. No.: WO2010/114013
PCT Pub. Date: Oct. 7, 2010

(65) Prior Publication Data
US 2012/0076836 A1    Mar. 29, 2012

(30) Foreign Application Priority Data
Mar. 31, 2009    (JP) ................. 2009-085176

(51) Int. Cl.
*A61K 9/14*    (2006.01)
*C07H 21/02*   (2006.01)
*C12N 15/11*   (2006.01)

(52) U.S. Cl.
USPC ................... 424/486; 536/24.5; 514/44 A

(58) Field of Classification Search
None
See application file for complete search history.

(56) References Cited

U.S. PATENT DOCUMENTS
2001/0000510 A1   4/2001  Sakurai et al.

FOREIGN PATENT DOCUMENTS

| | | |
|---|---|---|
| EP | 0 721 776 A1 | 7/1996 |
| JP | 2690276 B2 | 8/1997 |
| JP | 2008-201673 A | 9/2008 |
| WO | WO 2005/078084 A1 | 8/2005 |
| WO | WO 2006/123631 A1 | 11/2006 |

OTHER PUBLICATIONS

Itaka et al (J. Am. Chem. Soc. 2004, 126, 13612-13613, with supporting information).*
Qi et al (Am J Physiol Renal Physiol 291: F1070-F1077, 2006).*
Itaka et al., *Biomaterials*, 24: 4495-4506 (2003).
Matsumoto et al., *Biomacromolecules*, 10: 119-127 (2009).
European Patent Office, Extended European Search Report in European Patent Application No. 10758784.2 (Sep. 12, 2012).
Huang, *Polymer Materials Sciences & Engineering*, 25(1): 1-4 (2009).
Akhtar et al., *The Journal of Clinical Investigation*, 117(12): 3623-3632 (2007).
Bitko et al., *Nature Medicine*, 11(1): 50-55 (2005).
Blow, Nathan, *Nature*, 450: 1117-1120 (2007).
Derouchey et al., *Biomacromolecules*, 9: 724-732 (2008).
Gewirtz, Alan M., *The Journal of Clinical Investigation*, 117(12): 3612-3614 (2007).
Kim et al., *Nature Reviews Genetics*, 8: 173-184 (2007).
Nishiyama et al., *Polymer Reprints*, Japan, 57(2): 2769-2770 (2008).
Palliser et al., *Nature*, 439: 89-94 (2006).
Savaskan et al., *Nature Medicine*, 14(6): 629-632 (2008).
Shimizu et al., *J. Am. Soc. Nephrol.*, 21: 622-633 (2010).
Soutschek et al., *Nature*, 432: 173-178 (2004).
Thakker et al., *Proc. Natl. Acad. Sci. U.S.A.*, 101: 17270-17275 (2004).
Tuffin et al., *J. Am. Soc. Nephrol.*, 16: 3295-3305 (2005).
Zimmermann et al., *Nature*, 441: 111-114 (2006).
Japanese Patent Office, International Search Report in International Patent Application No. PCT/JP2010/055826 (May 25, 2010).
Castanotto et al., *Nature*, 457: 426-433 (Jan. 22, 2009).
Jiang et al., *Nature Nanotechnology*, 3: 145-150 (Mar. 2008).
Minchin, Rod, *Nature Nanotechnology*, 3: 12-13 (Jan. 2008).

* cited by examiner

*Primary Examiner* — Richard Schnizer
(74) *Attorney, Agent, or Firm* — Leydig, Voit & Mayer, Ltd.

(57) ABSTRACT

Provided are a delivery system that is useful in delivering a double-stranded ribonucleic acid that functions in gene silencing in glomeruli, particularly in mesangial cells and the like, to the tissue or cells, and the like. A polyion complex in the form of a non-polymeric micelle consisting of a double-stranded ribonucleic acid and a block copolymer represented by the formula (I) or (II) below, which are electrostatically bound together, wherein the polyion complex has an average particle diameter of less than 100 nm as measured by a dynamic light scattering measuring method:

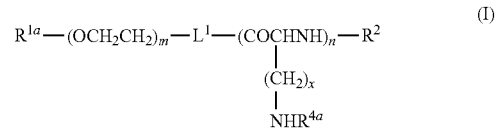

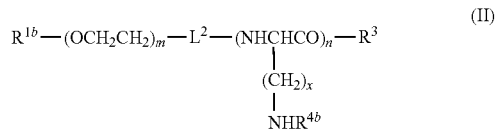

wherein each symbol is as defined in the specification.

11 Claims, 20 Drawing Sheets

PEG-PLL:

Electrostatic interaction and self-assembly

P(Asp):     or    siRNA siRNA concentration: 10 μM, Buffer: 10mM Hepes pH 7.3, temperature: 25°C

| Scattered light intensity | Polydispersion index | Cumulant diameter/nm | Zeta potential/mV |
|---|---|---|---|
| 966 | 0.52 | 130 | +2.8 |

Cy3-siRNA concentration: 50nM, polymer: PEG-PLL 12-73, Buffer: 10mM Hepes pH 7.3

| N/P | Diffusion time ($\mu$ sec) | Fluid dynamic diameter (nm) |
|---|---|---|
| 0 | 103.2±1.1 | 6.56±0.07 |
| 0.7 | 193.1±2.2 | 12.3±0.10 |
| 1.4 | 215.1±2.0 | 13.7±0.13 |
| 2.1 | 184.3±2.0 | 11.7±0.13 |
| 2.8 | 182.8±1.9 | 11.6±0.12 |

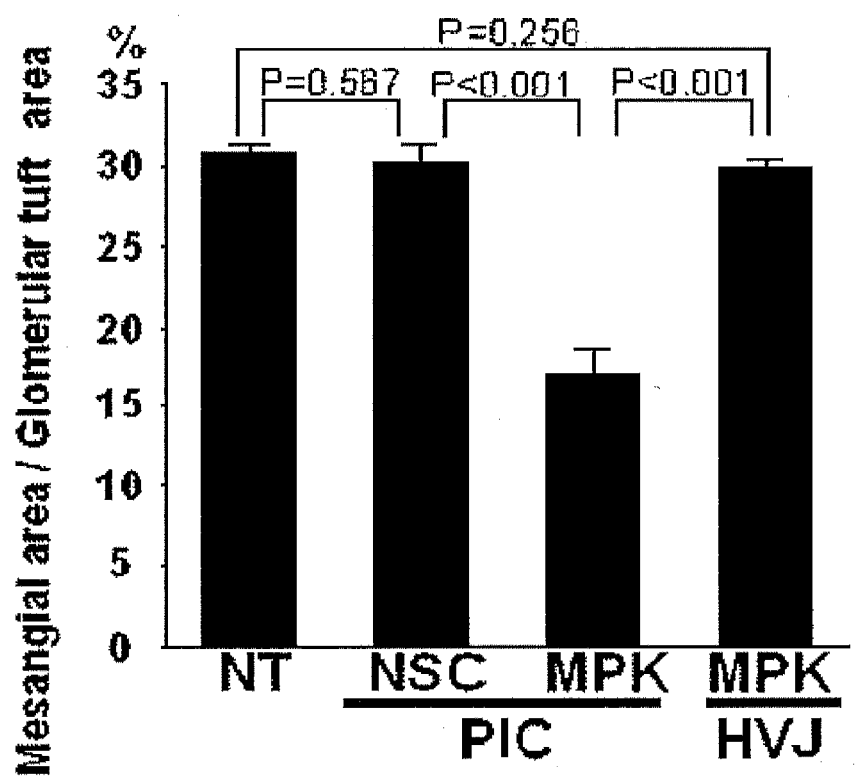

A

B

POLYION COMPLEX OF DOUBLE-STRANDED RIBONUCLEIC ACID

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 1,057 bytes ASCII (Text) file named "708987SequenceListing.txt," created Sep. 23, 2011.

TECHNICAL FIELD

The present invention relates to a polyion complex of double-stranded ribonucleic acid, specifically to the in vivo delivery of ribonucleic acids, more specifically to a drug delivery system for ribonucleic acid drugs.

BACKGROUND ART

RNA interference with a double-stranded short interfering RNA (siRNA) is highly promising not only as a research tool, but also as a therapeutic strategy, with its potent capacity of gene silencing (Non-patent Documents 1 to 4). However, applying siRNAs in vivo remains limited to topical delivery (Non-patent Documents 5 to 8). This limitation is attributable to the low stability of siRNA due to enzymatic decomposition in vivo and/or the low permeability of the cell membrane. While development of a delivery vehicle will possibly definitely enable the introduction of siRNA into target tissue by systemic administration, only a few reports are available on delivery systems which take advantage of the efficacy of siRNA on renal diseases.

A lipid-conjugated siRNA (Non-patent Document 9) or a liposome-encapsuled siRNA (Non-patent Document 10) has been shown to be accumulated in the liver and silence the target gene; however, the renal distribution of the siRNA is thought to be nothing more than watching the degradation process in tubular cells or the process of excretion into tubular lumen. Characterized by the secretion of a wide variety of pathogenic factors by resident cells in response to hemodynamic or immunological derangements, the glomerulus is a reasonable target for molecular therapy. However, an siRNA alone (a small molecule several nanometers long) is quickly excreted in the urine, whereas the above-described lipid-conjugated siRNA or liposome-encapsuled siRNA is difficult to deliver to mesangial cells and the like which are connective tissue in glomeruli, because of its size (several hundred nanometers) and characteristics. Against this background with the low availability of effective drugs for renal diseases, there is a demand for the development of a delivery system suitable for glomerulus-targeted gene silencing with siRNA.

The present inventors previously reported that a polyion complex with a block copolymer is useful as a delivery system for charged proteins and DNAs (Patent Document 1). The present inventors also investigated structures of block copolymers and methods of preparing a polyion complex that are particularly suitable for the delivery of double-stranded oligonucleic acids, and reported a block copolymer carrying a double-stranded oligonucleic acid in the form of a polymeric micelle (Patent Document 2). It was also reported that a complex of a carrier having as a side chain a hydrophilic group bound to a polycationic compound in the form of a comb (graft copolymer) and an RNA improves the stability and retentivity of the RNA in the blood (Patent Document 3). The nucleic acid delivery systems described in Patent Documents 1 and 2 are expected to ensure stable delivery to various tissues in vivo, and are polymeric micelles having a size distribution of several tens to several hundreds of nanometers. The complex described in Patent Document 3 is shown to potently suppress gene expression in the liver, but there is no description of delivery to kidney regions.

PRIOR ART DOCUMENTS

[Patent Documents]
Patent Document 1: JP-B-2690276
Patent Document 2: WO2005/078084
Patent Document 3: JP-A-2008-201673
[Non-patent Documents]
Non-patent Document 1: Gewirtz, A. M. 2007. J. Clin. Invest. 117:3612-3614
Non-patent Document 2: Akhtar, S., and Benter, I. F. 2007. J Clin. Invest. 117:3623-3632
Non-patent Document 3: Blow, N. 2007. Nature. 450:1117-1120
Non-patent Document 4: Kim, D. H., and Rossi, J. J. 2007. Nat. Rev. Genet. 8:173-184
Non-patent Document 5: Savaskan, N. E., et al. 2008. Nat. Med. 14:629-632
Non-patent Document 6: Palliser, D., et al. 2006. Nature. 439:89-94
Non-patent Document 7: Thakker, D. R., et al. 2004. Proc. Natl. Acad. Sci. U.S.A. 101:17270-17275
Non-patent Document 8: Bitko, V., Musiyenko, A., Shulyayeva, O., and Barik, S. 2005. Nat. Med. 11:50-55
Non-patent Document 9: Soutschek, J., et al. 2004. Nature. 432:173-178
Non-patent Document 10: Zimmermann, T. S., et al. 2006. Nature. 441:111-114

SUMMARY OF THE INVENTION

Problems to be Solved by the Invention

The present invention has been developed in view of the above-described problems, and is intended to provide a delivery system that is useful in delivering a double-stranded ribonucleic acid that functions in gene silencing in glomeruli, particularly in mesangial cells and the like, to the tissue or cells, and the like.

Means of Solving the Problems

The present inventors conducted extensive investigations to solve the above-described problems, and found that by mixing a double-stranded ribonucleic acid and a block copolymer having a particular polycation structure under specified conditions, a polyion complex of smaller size, having an average particle diameter of less than 100 nm, is produced without forming a polymeric micelle, then succeeded for the first time in effectively delivering a double-stranded ribonucleic acid to glomerular cells using such a polyion complex, and have developed the present invention.

Accordingly, the present invention is as follows:

[1] A polyion complex in the form of a non-polymeric micelle consisting of a double-stranded ribonucleic acid and a block copolymer represented by the formula (I) or (II) below, which are electrostatically bound together, wherein the polyion complex has an average particle diameter of less than 100 nm as measured by a dynamic light scattering measuring method:

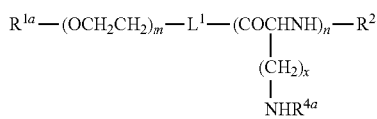

(I)

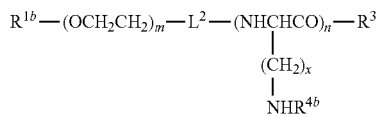

(II)

(in the formulas above, each of $R^{1a}$ and $R^{1b}$ independently represents a hydrogen atom or an unsubstituted or substituted linear or branched $C_{1-12}$ alkyl group, each of $L^1$ and $L^2$ represents a linkage group, $R^2$ represents a hydrogen atom, a protecting group, a hydrophobic group or a polymerizing group, $R^3$ represents a hydroxyl group, an oxybenzyl group, an —NH—$(CH_2)_a$—X group (X is an amine compound residue comprising one kind or two kinds or more of a primary, secondary or tertiary amine or a quaternary ammonium salt, or a non-amine compound residue; a is an integer of 1 to 5) or an initiator residue, each of $R^{4a}$ and $R^{4b}$ independently represents a hydrogen atom, a protecting group for amino group or —C(=NH)$NHR^5$ ($R^5$ represents a hydrogen atom or a protecting group for amino group), m represents an integer of 5 to 20000, n represents an integer of 2 to 5000, and x represents an integer of 1 to 5).

[2] The polyion complex described in [1] above, wherein the double-stranded ribonucleic acid is an siRNA.

[3] The polyion complex described in [1] or [2] above, which has an average particle diameter of less than 50 nm.

[4] The polyion complex described in any one of [1] to [3] above, which has an average particle diameter of 10 to less than 20 nm.

[5] A pharmaceutical composition comprising the polyion complex described in any one of [1] to [4] above and a pharmaceutically acceptable carrier.

[6] The pharmaceutical composition described in [5] above, which is to be delivered to a glomerulus or mesangial cell.

[7] The pharmaceutical composition described in [5] or [6] above, which is to be used to treat or prevent renal diseases whose pathologic condition occurs mainly in mesangium.

[8] A kit for preparing a polyion complex nanocarrier for delivering a double-stranded ribonucleic acid, consisting of a block copolymer represented by the general formula (I) or (II) below:

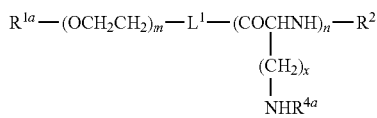

(I)

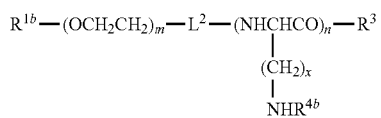

(II)

(in the formulas above, each of $R^{1a}$ and $R^{1b}$ independently represents a hydrogen atom or an unsubstituted or substituted linear or branched $C_{1-12}$ alkyl group, each of $L^1$ and $L^2$ represents a linkage group, $R^2$ represents a hydrogen atom, a protecting group, a hydrophobic group or a polymerizing group, $R^3$ represents a hydroxy group, an oxybenzyl group, an —NH—$(CH_2)_a$—X group (X is an amine compound residue comprising one kind or two kinds or more of a primary, secondary or tertiary amine or a quaternary ammonium salt, or a non-amine compound residue; a is an integer of 1 to 5) or an initiator residue, each of $R^{4a}$ and $R^{4b}$ independently represents a hydrogen atom, a protecting group for amino group or —C(=NH)$NHR^5$ ($R^5$ represents a hydrogen atom or a protecting group for amino group), m represents an integer of 5 to 20000, n represents an integer of 2 to 5000, x represents an integer of 1 to 5), and a reagent for dissolving the block polymer and/or double-stranded ribonucleic acid, housed in separate containers.

[9] The kit described in [8] above, which further comprises a container housing a double-stranded ribonucleic acid.

[10] The kit described in [8] or [9] above, which further comprises an instruction sheet stating that the block copolymer and the double-stranded ribonucleic acid be mixed in a ratio of N/P=1.2 to 1.5 (N represents the total number of cations in the block copolymer; P represents the total number of phosphoester bonds or equivalent bonds in the double-stranded ribonucleic acid).

[11] The kit described in any one of [8] to [10] above, which is to be used for delivery to glomeruli or mesangial cells.

[12] A method for treating or preventing a renal disease comprising a step of administering the pharmaceutical composition described in any one of [5] to [7] above to a subject in need thereof.

[13] The method described in [12] above, wherein the renal disease is a renal disease pathologically characterized mainly by mesangium.

Effect of the Invention

According to the present invention, it is possible to provide a polyion complex having a much smaller average particle diameter of less than 100 nm (preferably less than 50 nm, more preferably 10 to less than 20 nm) than conventional submicron-sized nanocarriers and polyion complexes that have been developed so far by the present inventors. The polyion complex of the present invention is obtained as a complex formed by a double-stranded ribonucleic acid and a block copolymer via electrostatic binding, and as a nanocarrier of double-stranded ribonucleic acid whose size is less than 100 nm (preferably less than 50 nm, more preferably 10 to less than 20 nm), it enables easy and efficient delivery to in vivo tissues which conventional submicron-sized nanocarriers and the like are unable to reach (for example, glomeruli or mesangial cells).

The pharmaceutical composition of the present invention, thanks to the above-described features of the polyion complex component, can be stably circulated in the blood for a long time without being rapidly excreted in the urine. Therefore, a gene silencing effect is sustained in the treatment or prophylaxis of a disease by utilizing gene silencing with a double-stranded ribonucleic acid such as an siRNA, which in turn not only allows the effect to be exhibited even with low doses, but also offers expectations for expansion of the range of options for the treatment or prophylaxis of renal diseases whose pathologic condition occurs mainly in mesangium for which few effective drugs have been available so far.

According to the kit of the present invention, a polyion complex having a very small size of less than 100 nm (preferably less than 50 nm, more preferably 10 to less than 20 nm) can easily be prepared.

BRIEF DESCRIPTION OF THE DRAWINGS

[FIG. 7E] A histological analysis of renal sections showing amelioration of glomerular lesions by MAPK1 siRNA/PIC nanocarrier. PAS-positive glomeruli lesions (%) decreased significantly in the group treated with MAPK1 siRNA/PIC nanocarrier. P-values were calculated by ANOVA. Mean+/−s.e., n=6.

MODES FOR EMBODYING THE INVENTION

Figure 1A:
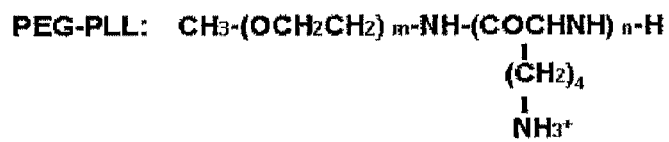
[FIG. 1A] Shown are the chemical structures of the poly(ethylene glycol)-poly(L-lysine) (PEG-PLL) block copolymer and poly($\alpha,\beta$-aspartic acid) [P(Asp)] homopolymer used in Examples.
Figure 1A:
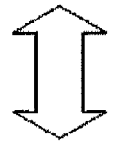
Figure 1A:
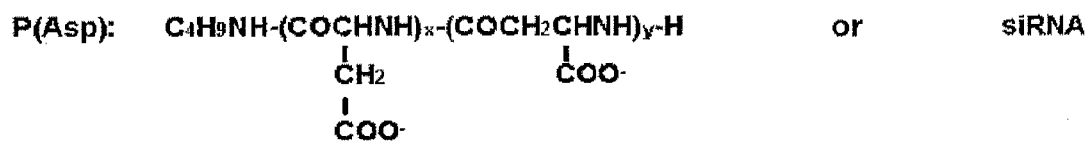

The present invention provides a polyion complex in the form of a non-polymeric micelle, consisting of a double-stranded ribonucleic acid and a block copolymer which are electrostatically bound together.

1. Block Copolymer

The block copolymer used in the present invention is represented by the general formula (I) or (II) below.

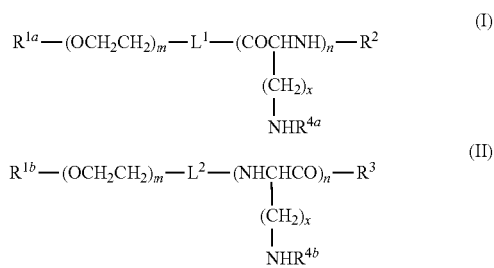

(in the formulas above,
each of $R^{1a}$ and $R^{1b}$ independently represents a hydrogen atom or an unsubstituted or substituted linear or branched $C_{1-12}$ alkyl group,
each of $L^1$ and $L^2$ represents a linkage group,
$R^2$ represents a hydrogen atom, a protecting group, a hydrophobic group or a polymerizing group,
$R^3$ represents a hydroxy group, an oxybenzyl group, an —NH—$(CH_2)_a$—X group (X is an amine compound residue comprising one kind or two kinds or more of a primary, secondary or tertiary amine or a quaternary ammonium salt, or a non-amine compound residue; a is an integer of 1 to 5) or an initiator residue, each of $R^{4a}$ and $R^{4b}$ independently represents a hydrogen atom, a protecting group for amino group or —C(=NH)NHR$^5$ (R$^5$ represents a hydrogen atom or a protecting group for amino group),
m represents an integer of 5 to 20000, n represents an integer of 2 to 5000, x represents an integer of 1 to 5)

The block copolymer used in the present invention is a copolymer of the formula (I) or (II) consisting of a polyethylene glycol (hereinafter sometimes abbreviated as "PEG"), or a derivative portion thereof, that constitutes a non-chargeable segment as the left half, and a polyamino acid having a primary amino group in the side chain thereof, that constitutes a charged segment as the right half, which segments are bound via a linkage group ($L^1$ or $L^2$). Such a charged segment and a double-stranded ribonucleic acid form a polyion complex (hereinafter sometimes abbreviated as "PIC").

A preferable molecular weight of the PEG, or a derivative thereof, that constitutes the non-charged segment is 200 to 1,000,000, more preferably 500 to 200,000, particularly preferably 1,000 to 50,000.

A preferable molecular weight of the polyamino acid that constitutes the charged segment is 200 to 1,000,000, more preferably 500 to 200,000, particularly preferably 1,000 to 50,000.

With regard to the general formula (I) or (II) above, each of $R^{1a}$ and $R^{1b}$ independently represents a hydrogen atom or an unsubstituted or substituted linear or branched $C_{1-12}$ alkyl group; $C_{1-12}$ alkyls include methyl, ethyl, n-propyl, iso-propyl, n-butyl, sec-butyl, tert-butyl, n-pentyl, n-hexyl, decyl, undecyl and the like. In the case of substitutions, substituents include acetalized formyl groups, cyano groups, formyl groups, carboxyl groups, amino groups, $C_{1-6}$ alkoxycarbonyl groups, $C_{2-7}$ acylamide groups, identical or different tri-$C_{1-6}$ alkylsiloxy groups, siloxy groups or silylamino groups.

$R^2$ in the general formula (I) represents a hydrogen atom, a protecting group or a hydrophobic group; protecting groups include $C_{1-6}$ alkyl carbonyl groups, with preference given to acetyl groups. Hydrophobic groups include derivatives of benzene, naphthalene, anthracene, pyrene and the like.

Methods of introducing these protecting groups, hydrophobic groups, and polymerizing groups into an end of a copolymer include techniques in use for ordinary synthesis, such as methods using acid halides, methods using acid anhydrides, and methods using active esters.

$R^3$ in the general formula (II) is a hydroxy group, an oxybenzyl group, or an —NH—$(CH_2)_a$—X group. Here, X is an amine compound residue comprising one kind or two kinds or more of a primary, secondary or tertiary amine or a quaternary ammonium salt, or a non-amine compound residue; a is an integer of 1 to 5. Alternatively, $R^3$ is an initiator residue. Hence, when a block copolymer is produced by a method in which an N-carboxylic anhydride of a protecting amino acid is polymerized using a low molecular initiator to synthesize a polyamino acid segment, which is then bound to a PEG segment, the block copolymer may assume a structure derived from the initiator used, that is, —NH—$R^6$ wherein $R^6$ is an unsubstituted or substituted linear or branched $C_{1-20}$ alkyl group.

Unsubstituted or substituted linear or branched $C_{1-20}$ alkyl groups include $C_{1-6}$ lower alkyls such as methyl, ethyl, n-propyl, iso-propyl, n-butyl, tert-butyl, n-pentyl, and n-hexyl, as well as $C_{7-12}$ intermediate alkyls and $C_{13-20}$ higher alkyls such as tetradecyl, hexadecyl, octadecyl, and icosanyl. In some cases, these groups may be substituted by one or more halogens (for example, fluorine, base, bromine) and, in the case of intermediate to higher alkyls, may be substituted by one hydroxy group.

Each of $R^{4a}$ and $R^{4b}$ in the general formula (I) or (II) is independently a hydrogen atom, a protecting group for amino group or —C(=NH)NHR$^5$ ($R^5$ represents a hydrogen atom or a protecting group for amino group). A protecting group in $R^{4a}$, $R^{4b}$ and $R^5$ normally means a group for use as a protecting group for amino group; examples include Z group, Boc group, acetyl group, trifluoroacetyl group and the like. It is preferable that the protecting group be removed before forming a polyion complex with a double-stranded nucleic acid. Therefore, it is preferable that a major portion (for example, 90% or more, preferably 95% or more, more preferably 99% or more) of $R^{4a}$, $R^{4b}$ and $R^5$ in the general formula (I) or (II) be a hydrogen atom.

Defining the chain length of the non-charged segment, m is an integer of 5 to 20000, preferably 10 to 5000, particularly preferably 40 to 500. Defining the chain length of the charged segment, n is an integer of 2 to 5000, preferably an integer of 4 to 2500, more preferably 5 to 1000, particularly preferably 10 to 200. As far as the copolymer of the general formula (I) or (II) and a double-stranded ribonucleic acid form a polyion complex, m and n are not limited. Therefore, although designations such as polyethylene glycol and polyamino acid are used herein for the sake of convenience, the term "poly" is used as a concept encompassing what are categorized under so-called "oligo".

Defining the side chain of the polyamino acid in the general formula (I) or (II), x is an integer of 1 to 5, preferably 2 to 4, particularly preferably 3 (corresponding to an ornithine side chain) or 4 (corresponding to a lysine side chain). In cases where x is 3 and $R^{4a}$ and $R^{4b}$ are —C(=NH)NH$_2$, the side chain corresponds to an arginine side chain.

In the present invention, a preferred block copolymer is a polyethylene glycol-polylysine block copolymer (abbreviated as PEG-PLL) obtained by reacting a polyethylene glycol having a primary amino group at one end and an Nε-Z-L-lysine N carboxylic anhydride, and then removing the Z group. Besides, a polyethylene glycol-polyornithine block copolymer (abbreviated as PEG-PLO) can also be used suitably.

The method of producing the above-described copolymer is not particularly limited; a useful method is, for example, a method wherein the copolymer of the present invention is prepared by polymerizing, using a PEG derivative having an amino group at one end, an N-carboxylic anhydride of a protecting amino acid such as Nε-Z-L-lysine to the amino end to synthesize a block copolymer, and then converting the side chain. In this case, the copolymer assumes the structure represented by the general formula (I), and the linkage group $L^1$ assumes a structure derived from a terminal structure of the PEG derivative and the like used, with preference given to $(CH_2)_b$—NH— wherein b is an integer of 0 to 5.

The copolymer of the present invention can also be produced by using a method wherein a polyamino acid segment moiety is first synthesized and then bound to a PEG segment moiety; in this case, the resulting structure is identical to that produced by the above-described method in some cases, or is the structure of the general formula (II) in other cases. The linkage group $L^2$ is not particularly limited, and is preferably $(CH_2)_c$—CO— wherein c is an integer of 0 to 5.

The above-described block copolymer can be produced by a publicly known method. Preferred methods of production include, for example, methods described in the official gazette for Japanese Patent 2690276 and the pamphlet of WO No. 2005/078084.

2. Double-stranded Ribonucleic Acid

In the present invention, the nucleic acid to be electrostatically bound to the above-described block copolymer may be any kind of double-stranded nucleic acid, as far as it is substantially a ribonucleic acid. Hence, the double-stranded ribonucleic acid in the present invention refers to one with a nucleoside comprising a ribose, rather than a deoxyribose, as the primary constituent, wherein a nucleic acid with nucleosides polymerized via a phosphoester bond or an equivalent bond can assume a double-stranded structure. The double-stranded structure is exemplified by, but is not limited to, a double strand formed by single-stranded ribonucleic acids via a complementary base-pairing, a hairpin structure formed by a complementary base sequence in a single-stranded ribonucleic acid, and the like. The double-stranded ribonucleic acid is often used with the aim of having a "gene knockdown" effect to suppress the expression of a particular gene in specified cells; such nucleic acids for knockdown include, but are not limited to, siRNAs, shRNAs and the like. The siRNA sometimes has a DNA overhang at the 5' end and/or 3' end thereof. The nucleic acid is sometimes an RNA-DNA hybrid nucleic acid, and another nucleic acid derivative is sometimes present in the double-stranded ribonucleic acid. Furthermore, to visualize the behavior in a living organism, a labeled double-stranded ribonucleic acid is sometimes used. Such cases are also included in the scope of the double-stranded ribonucleic acid in the present invention, as far as the nucleic acid that substantially constitutes the double strand is a ribonucleic acid. The length of the double-stranded ribonucleic acid is not particularly limited, as far as the specified purpose is accomplished in cells, and is 10 to 1000 nucleotides (nt), preferably 10 to 100 nt, more preferably 15 to 50 nt.

Recently, a phenomenon in which double-stranded RNA causes gene knockdown was discovered and named RNA interference (RNAi). It has been shown that siRNAs and shRNAs destroy mRNAs not only in flies and nematodes, but also in mammalian cells. An siRNA (short interference RNA, small interfering RNA) is a short double-stranded RNA having a sequence complementary to the gene to be targeted, possessing the action of potently suppressing the expression of the gene to be targeted. An shRNA (short hairpin RNA) comprises a sense strand and an antisense strand which are joined via a loop, and it becomes an siRNA via processing in cells before manifesting a knockdown effect. Also, miRNAs (micro RNAs), which were recently discovered as an endogenous gene expression regulatory mechanism, have been shown to often lack complete complementarity to target mRNA, despite a putative mechanism similar to that of siRNAs. Therefore, complete complementarity of the siRNA to the target sequence is not always an absolute requirement. The length of the siRNA is 10 to 100 nucleotides (nt), preferably 10 to 50 nt, more preferably 18 to 25 nt.

3. Polyion Complex

A method of producing a polyion complex of the above-described double-stranded ribonucleic acid and block copolymer is based on mixing respective solutions in an appropriate mixing ratio to allow the nucleic acid to electrostatically bind to the block copolymer. Hence, when the nucleic acid and block copolymer are mixed together, an electrostatically bound polyion complex is formed due to the negative charge of the nucleic acid and the positive charge of the block copolymer. In the present invention, by limiting the choice of the nucleic acid to be bound to the above-described block copolymer to a double-stranded ribonucleic acid, a polyion complex in the form of a non-polymeric micelle can be generated. Here, the form of a polymeric micelle refers to a core-shell type form wherein the hydrophilic segment of the block copolymer (PEG or a derivative moiety thereof) forms a shell moiety and the hydrophobic segment (polyamino acid moiety) forms a core moiety. The block copolymer used in the present invention does not form a core-shell type form because of the electrostatic interaction between the cation in the polyamino acid moiety and the anion in the double-stranded ribonucleic acid. Therefore, the form of a non-polymeric micelle means not being the above-described core-shell type form.

The mixing ratio of double-stranded ribonucleic acid and block copolymer can be expressed by the ratio of the total number of cations in the block copolymer (N) and the total number of phosphoester bonds or equivalent bonds in the double-stranded ribonucleic acid (P) (N/P ratio). Here, a bond equivalent to a phosphoester bond refers to a bond formed between some nucleosides in the ribonucleic acid in order to increase the stability in vivo in terms of greater nuclease resistance than phosphoester bond and the like; such bonds include phosphorothioate, phosphorodithioate, phosphoroamidate, boranophosphate, phosphoroselenate, methylphosphoroate and the like. When the above-described equivalent bond has a charge equivalent to that of phosphoester bond (−1), P can be obtained by summing the numbers of the two; in cases where no charge is present (0), in cases where a positive charge is present (+1), or in cases where two negative charges are present (−2), P can be calculated by deleting and adding each charge from the total number (N) of phosphoester bonds. The total number of cations in the block copolymer (N) is the total number of cationic amino groups in the formula (I) or (II) above.

The N/P ratio is not limited, as far as a polyion complex can be formed. However, because free double-stranded ribonucleic acids that do not form a complex increase with the increase in P, and also because empty block copolymers that do not bind to the double-stranded ribonucleic acid increase with the increase in N, those skilled in the art are able to choose an appropriate N/P ratio. When the purpose is to efficiently deliver a double-stranded ribonucleic acid, the N/P ratio is preferably 1.2 to 1.5, more preferably 1.2 to 1.4.

Solutions useful in forming a polyion complex include physiological saline, phosphate-buffered physiological saline (PBS) and the like. The double-stranded ribonucleic acid and block copolymer are separately dissolved in the above-described solution; the double-stranded ribonucleic acid solution and block copolymer solution obtained are mixed together, and the mixture is normally allowed to stand, or stirred, at 4 to 25° C. for 0.5 to 24 hours, to form a polyion complex. Furthermore, operations such as dialysis, agitation, dilution, concentration, sonication, temperature control, pH control, ionic strength control, and addition of organic solvent can be added as appropriate.

The polyion complex of the present invention thus formed has an average particle diameter of less than 100 nm as measured by a dynamic light scattering measuring method. The average particle diameter is preferably less than 50 nm, more preferably 10 to 20 nm, most preferably 10 to less than 20 nm. The average particle diameter can be measured by, for example, generating a particle size distribution curve using a dynamic light scattering photometer (e.g., model DLS-7000DH, manufactured by Otsuka Electronics Co., Ltd.), and performing a histographic analysis. When the double-stranded ribonucleic acid is fluorescently labeled, the average particle diameter may be measured by fluorescence correlation spectroscopy. A method of measuring the average particle diameter by fluorescence correlation spectroscopy is described in Examples shown below.

4. Pharmaceutical Composition

A pharmaceutical composition comprising the polyion complex of the present invention and a pharmaceutically acceptable carrier can be used as a pharmaceutical intended for gene therapy by using an electrostatically bound double-stranded ribonucleic acid as an active ingredient.

After being blended with a pharmaceutically acceptable carrier, the pharmaceutical composition of the present invention can be administered parenterally as a venous, subcutaneous, or intramuscular injection. In this case, the composition can be prepared as a freeze-dried product as required by a method known per se. As the pharmacologically acceptable carrier, various organic or inorganic carrier substances in common use as pharmaceutical materials can be used, which are mixed as solvents, solubilizers, suspending agents, isotonizing agents, buffers, soothing agents and the like. Pharmaceutical additives such as antiseptics, antioxidants, and colorants can also be used as necessary. Examples of suitable solvents include water for injection, alcohols, propylene glycol, macrogol, sesame oil, corn oil and the like. Examples of suitable solubilizers include polyethylene glycol, propylene glycol, D-mannitol, benzyl benzoate, ethanol, trisaminomethane, cholesterol, triethanolamine, sodium carbonate, sodium citrate and the like. Examples of suitable suspending agents include surfactants such as stearyltriethanolamine, sodium lauryl sulfate, laurylaminopropionic acid, lecithin, benzalkonium chloride, benzethonium chloride, and glyceryl monostearate; hydrophilic polymers such as polyvinyl alcohol, polyvinylpyrrolidone, carboxymethylcellulose sodium, methylcellulose, hydroxymethylcellulose, hydroxyethylcellulose, and hydroxypropylcellulose. Examples of suitable isotonizing agents include sodium chloride, glycerin, D-mannitol and the like. Examples of suitable buffers include buffer solutions such as of phosphates, acetates, carbonates and citrates, and the like. Examples of suitable soothing agents include benzyl alcohol and the like. Examples of suitable antiseptics include para-oxybenzoate, chlorobutanol, benzyl alcohol, phenethyl alcohol, dehydroacetic acid, sorbic acid and the like. Examples of suitable antioxidants include sulfites, ascorbic acid and the like.

A polyion complex having an average particle diameter of less than 100 nm is favorable in that it can be recovered at extremely high yields to enable efficient supply of injections, even when subjected to eradicating filtration using a 0.22 μm filter for use in preparing injections (for subcutaneous injection, for venous injection, for arterial injection, for intramuscular injection, for intraperitoneal injection and the like).

Figure 12A:
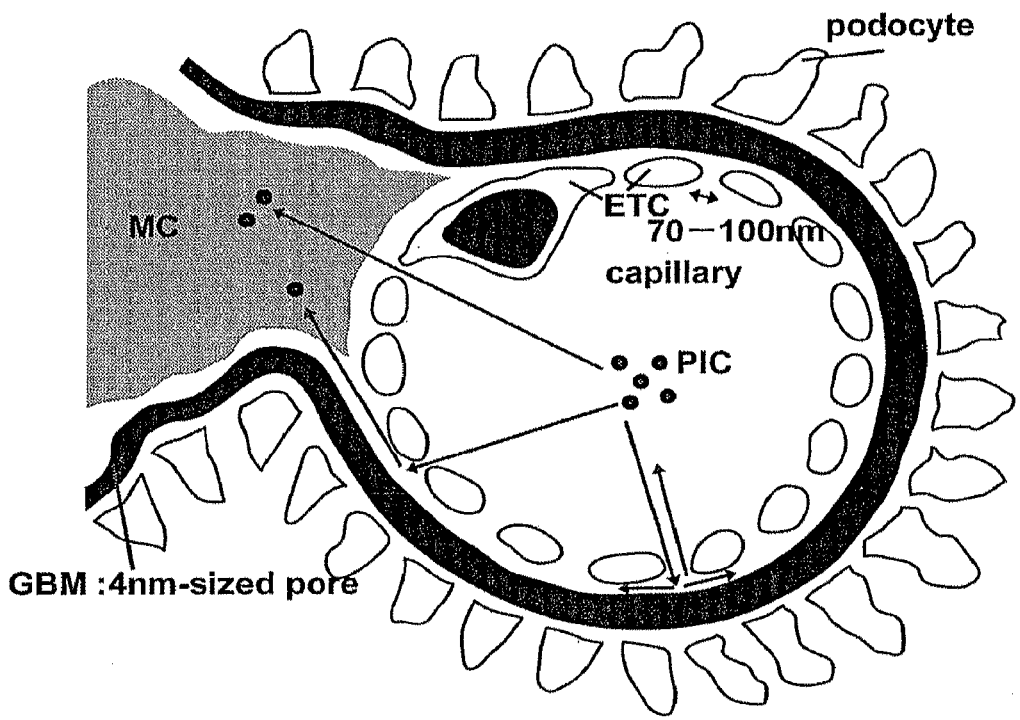
[FIG. 12A] A schematic drawing showing a cross-sectional view of glomerulus and the PIC nanocarrier (PIC) of the present invention. In the figure, MC stands for a mesangial cell, ETC for a glomerular endothelial cell, GBM for glomeruli basement membrane, podocyte for a podocyte, and capillary for a capillary blood vessel.
Figure 12B:
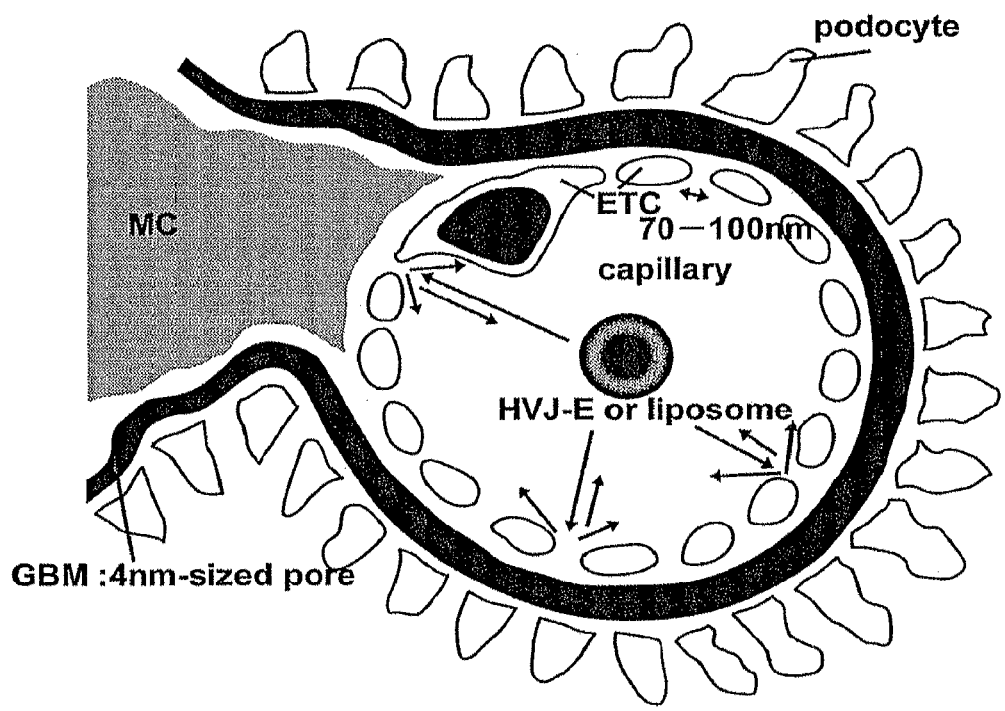
[FIG. 12B] A schematic drawing showing a cross-sectional view of a glomerulus, HVJ-E and liposome. In the figure, MC stands for a mesangial cell, ETC for a glomerular endothelial cell, GBM for glomeruli basement membrane, podocyte for a podocyte, and capillary for a capillary blood vessel.

A polyion complex having an average particle diameter of 10 to less than 20 nm can be efficiently delivered to glomeruli, to which its delivery has been difficult so far, particularly to mesangial cells. While passing the pores of glomerular endothelial cells (about 70 to 100 nm), the above-described polyion complex is unable to pass the glomerular basement membrane (gaps are open allowing substances about 4 nm in diameter to pass through). Because the basement membrane or septum does not interpose between glomerular endothelial cells and mesangial region, a polyion complex that has passed the glomerular endothelium is able to readily come in contact with mesangial cells, making it possible to deliver nucleic acid drugs to mesangial cells (FIG. 12A). For delivery systems whose particle diameter exceeds 200 nm, such as existing liposomes, particles are theoretically thought to be unable to pass the normally structured glomerular endothelium and the endothelial barrier in glomerular disease in its initial stage, when no morphological change is present, so that effective delivery to the mesangium cannot be achieved (FIG. 12B).

Dosage forms of the pharmaceutical composition of the present invention include injections; the composition can be administered intravenously, intra-arterially, intramuscularly, intra-articularly, subcutaneously, intradermally and the like. When delivery to the kidney is intended, continuous drip infusion via subcutaneous or intravenous route is desirable. Furthermore, a dosage form using a catheter can also be employed. In this case, the composition is normally provided in the form of a unit dosage ampule or multiple dosage container. The dose varies depending on the purpose of treatment, the recipient's age, route for administration, and frequency of administration, and can be changed over a wide range; the amount of double-stranded ribonucleic acid contained in the pharmaceutical composition of the present invention can be set as appropriate by those skilled in the art, and is, for example, 0.01 μg to 10000 μg per kg body weight per dose; doses are given at intervals of 3 days to 4 weeks.

The pharmaceutical composition of the present invention is excellent in stability in vivo and retentivity in the blood, and low in toxicity. The pharmaceutical composition of the present invention is useful as a therapeutic or prophylactic agent for diseases in mammals (e.g., humans, monkeys, horses, bovines, pigs, rabbits, rats, mice, dogs, cats and the like).

The disease targeted by the pharmaceutical composition of the present invention is not particularly limited, as far as it is a disease that can be treated by suppressing the expression of the gene to be targeted. As stated above, when the polyion complex contained in the pharmaceutical composition of the present invention has an average particle diameter of 10 to less than 20 nm, it is suitably used for treatment or prophylaxis of renal diseases whose pathologic condition occurs mainly in mesangium.

Renal diseases whose pathologic condition occurs mainly in mesangium include mesangial proliferative glomerulonephritis such as IgA nephropathy, with proliferative mesangial cells and increased mesangium matrix observed in membranous proliferative glomerulonephritis and connective tissue disease kidney. Meanwhile, diseases in which mesangial cells are thought to play a role in glomerulosclerosis include hypertensive nephrosclerosis, diabetic nephropathy and the like.

5. Kit

The present invention provides a kit for preparing a polyion complex nanocarrier for delivering a double-stranded ribonucleic acid. The kit comprises the above-described block copolymer and a reagent for dissolving the above-described block polymer and/or double-stranded ribonucleic acid, which are housed in separate containers. Dissolution reagents include, but are not limited to, physiological saline, PBS, Hepes buffer solution and the like, with preference given to RNase-free ones.

The kit may further comprise a container housing a particular double-stranded ribonucleic acid and/or a control double-stranded ribonucleic acid. The control for forming a polyion complex is not limited to a double-stranded ribonucleic acid, and may be a polyanion such as polyaspartic acid described in Examples below.

To prepare a polyion complex of double-stranded ribonucleic acid, it is preferable that a block copolymer and a double-stranded ribonucleic acid be mixed in a ratio of N/P=1.2 to 1.5 (N indicates the total number of cations in the block copolymer, P indicates the total number of phosphoester bonds or equivalent bonds in the double-stranded ribonucleic acid). Therefore, it is desirable that the kit of the present invention further comprise an instruction sheet describing these mixing conditions.

The polyion complex of double-stranded ribonucleic acid obtained using the kit of the present invention is useful as an investigational reagent in in vivo delivery, particularly in delivery to glomeruli or mesangial cells, in laboratory animals.

Laboratory animals for subjects of administration include, but are not limited to, mice, rats, guinea pigs, hamsters, rabbits, dogs, sheep, goat, bovines, pigs, monkeys and the like.

EXAMPLES

The present invention is hereinafter described in more detail by means of the following Examples and Test Examples, to which, however, the invention is never limited.

Laboratory Animals

Female BALB-c mice at 6 weeks of age and male Wistar rats at 4 weeks of age were purchased from Charles River Laboratories (Kanagawa, Japan); female MRL/lpr mice at 8 weeks of age were purchased from Japan SLC (Shizuoka, Japan). All mice and rats were reared with free access to autoclaved diet and sterilized water. All animal studies were conducted in compliance with the University of Tokyo's Principles of Guidelines for Animal Experiments.

Materials

α-Methoxy-ω-aminopoly(ethylene glycol) (PEG) (MW=12000) was obtained from NOF Corporation (Tokyo, Japan). A PEG-poly(L-lysine) (PEG-PLL) block copolymer (degree of polymerization of PLL: 72) was synthesized by ring-opening polymerization of an N-carboxylic anhydride (NCA) of an amino acid derivative, according to a previous report (Harada, A., Cammas, S., and Kataoka, K. 1996. Macromolecules. 29:6183-6188). HVJ-E was purchased from Ishihara Sangyo Kaisha, Ltd. (Osaka, Japan). A fluorescein isothiocyanate (FITC)-labeled poly(α,β-aspartic acid)

[FITC-P(Asp)] homopolymer (degree of polymerization of P(Asp): 26) was prepared by simple conjugation of FITC to the N-terminal primary amino group of P(Asp), according to a previous report (Nishiyama, N., and Kataoka, K. 2001. J. Control. Release. 74:83-94). A MAPK1 siRNA and a non-silencing control (scramble) siRNA were purchased from Qiagen. The sequences of the siRNAs were as follows:
Mm/Hs_MAPK1 (common to humans and mice):

```
                                (forward, SEQ ID NO: 1)
    5'-UGCUGACUCCAAAGCUCUGdTdT-3', (reverse, SEQ ID NO: 2)
    3'-dTdTACGACUGAGGUUUCGAGAC-5';
```

Non-silencing control siRNAs:

```
                                (forward, SEQ ID NO: 3)
    5'-UUCUCCGAACGUGUCACGUdTdT-3', (reverse, SEQ ID NO: 4)
    3'-dTdTAAGAGGCUUGCACAGUGCA-5'.
```

In some experiments, the non-silencing control siRNA was labeled with FITC, Alexa Fluor® 647, Cy3 or Cy5.

Preparation of PIC Nanocarrier

FITC-P(Asp) or siRNA and PEG-PLL (MW of PEG=12000; degree of polymerization of PLL: 72) were separately dissolved in 10 mM phosphate-buffered physiological saline (pH 7.4), and mixed in an N/P ratio [=(primary amino groups in PLL)/(carboxyl groups in P(Asp) or phosphate bond units in siRNA)]=1.4 to form a PIC nanocarrier (Itaka, K., et al. 2004. J. Am. Chem. Soc. 126:13612-13613; Ideta, R., et al. 2004. FEBS Lett. 557:21-25).

Preparation of HVJ Envelope Vector

A highly efficiently transforming HVJ-E vector was prepared as directed in the manufacturer's instruction manual.

Characterization of PIC nanocarrier

The average particle diameter and polydispersibility of the PIC nanocarrier were evaluated using a dynamic light scattering measuring apparatus (DLS) with the Zetasizer nanoseries (Malvern Insturements Ltd, UK) equipped with He—Ne laser (633 nm). Experiments by fluorescence correlation spectroscopy (FCS) were performed using LSM510 (Carl Zeiss, Germany) equipped with a 40× objective lens (C-apochromat, Carl Zeiss, Germany) and a ConfoCor3 module, to determine the size of the complex of PEG-PLL and siRNA. The irradiation source used was an Ar laser (488 nm) for Cy3-siRNA. Each sample was prepared from a mixture (1:200) of Cy3-siRNA and non-labeled siRNA in an 8-well Laboratory-Tek chamber (Nalgene Nunc International, Rochester, N.Y.) (final Cy3-siRNA concentration; 50 nM). Diffusion coefficient (D) was calculated on the basis of a Rhodamine 6G (50 nM) standard. Fluid dynamic diameter (d) was calculated from the Stokes-Einstein equation (d=$k_B$T/3 $\pi\eta$D, wherein $\eta$ is the viscosity of the solvent, $k_B$ is the Boltzmann constant, and T is absolute temperature).

Cell Culture and In Vitro Evaluation

Mouse mesangial cells were obtained by culturing glomeruli isolated from a kidney of a female MRL/lpr mouse at 8 weeks of age as reported previously (Okuda, T., Yamashita, N., Ogata, E., and Kurokawa, K. 1986. J. Clin. Invest. 78:1443-1448; Kaname, S., Uchida, S., Ogata, E., and Kurokawa, K. 1992. Kidney Int. 42:1319-1327), and maintained in a DMEM/F12 (50/50) medium containing 15% FCS, streptomycin (100 µg/ml), penicillin (100 U/ml) and L-glutamine (2 mM). The cells obtained exhibited a typical morphological profile of mesangial cells, being uniformly positive for smooth muscle a actin staining. Cells after 5 to 10 passages were used in the experiment shown below. To examine the intracellular uptake of the PIC nanocarrier by mesangial cells, 3 µl/well of the PIC nanocarrier (retaining FITC-labeled non-silencing control (scramble) siRNA) or naked FITC-labeled siRNA at a 50 nM concentration was applied to mouse mesangial cells subcultured in 0.4 ml per well of serum-containing medium on a chamber slide (8-well Lab-Tek™ Chamber Slides™, Nunc). Furthermore, using an Acrodisc syringe filter of 0.2 µm pore size (Pall Corporation, NY), the size barrier effect of the delivery vehicle was examined, and the siRNA/PIC nanocarrier and siRNA-incorporating HVJ-E were compared. To evaluate the gene silencing effect of the siRNA, siRNA/PIC nanocarrier (MAPK1 and non-silencing control siRNA) or naked MAPK1 siRNA was added to cultured mouse mesangial cells (1.0×10$^5$ cells/well) at various concentrations (5, 16, 50 or 160 nM). 24 hours later, the cells were used in the experiment shown below.

Accumulation of PIC Nanocarrier in the Kidney

To examine the accumulativity of PIC nanocarrier in the kidney, a FITC-P(Asp)/PIC nanocarrier (0.5 ml, 0.7 mg P(Asp) content), naked FITC-P(Asp) (0.5 ml, 0.7 mg) or FITC-P(Asp)/incorporating HVJ-E (0.5 ml, 0.7 mg P(Asp) content) was intraperitoneally administered to BALE-c mice. 6 hours after intraperitoneal injection, each mouse was autopsied. Tissue was instantaneously frozen using an OCT compound (Lab-Tek Products; Miles Laboratories, Naperville, Ill., USA); 4 µm frozen sections were prepared and examined using a fluorescence microscope (model BX51, Olympus, Tokyo, Japan). Regarding the accumulation of siRNA/PIC nanocarrier in the kidney, a Cy5-labeled siRNA/PIC nanocarrier (0.5 ml, 5 nmol siRNA content), Cy5-labeled naked siRNA (0.5 ml, 5 nmol) or Cy5-labeled siRNA-incorporating HVJ-E (0.5 ml, 5 nmol siRNA content) was administered to BALE-c mice. Each mouse was autopsied at 3.5 hours or 5.5 hours after the intraperitoneal injection. Tissue was instantaneously frozen using the OCT compound; 4 µm frozen sections were prepared and examined under a confocal laser scanning microscope (LSM 510, Carl Zeiss, Germany). To examine the intracellular localization of injected PIC nanocarrier in glomeruli, 1 ml of FITC-P(Asp)/PIC nanocarrier was administered to male Wistar rats at 4 weeks of age. At 120 minutes after tail vein injection, kidney tissue was extirpated and instantaneously frozen. 4 µm frozen sections were stained with an antibody against the mesangial cell-specific antigen Thy1.1 (clone MRC OX-7) (Serotec, Ltd., Oxford, England), and then detected using biotinylated anti-mouse IgG (secondary antibody; Dako Corp.) and Rhodamine/Neutralite Avidin (Southern Biotec, Birmingham, Ala.).

Stability and Urinary Excretion of PIC Nanocarrier in Mouse Plasma

To examine the stability of siRNA in the blood circulation, Alexa Fluor 647-labeled naked non-silencing siRNA, Alexa Fluor 647-labeled non-silencing siRNA/PIC nanocarrier or Alexa Fluor 647-labeled non-silencing siRNA-incorporating HVJ-E was intraperitoneally administered over time. The same amount of siRNA was used for all groups (0.5 ml, 5 nmol siRNA content). Subsequently, blood samples were collected from each mouse. The relative fluorescence unit (RFU) in sample plasma was examined using the Nanodrop ND-3300 fluorescence spectrophotometer (Nanodrop Technologies, Inc., DE), and % injection doses were calculated. The 100% injection dose was estimated using total blood volume based on mouse body weight. Alternatively, the stability of siRNA in plasma samples was examined directly by electrophoresis and ethidium bromide (EtBr) staining. Specifically, 50 μl of fresh mouse plasma was obtained and mixed with 350 μl of Tris-EDTA buffer solution. The siRNA was extracted from the reaction mixture using phenol/chloroform/isoamyl alcohol (25:24:1). The siRNA was electrophoresed on 5-20% polyacrylamide gel (Wako Pure chemical industries Ltd, Osaka, Japan) and stained with EtBr (0.1 μg/l), after which it was visualized by UV irradiation. Regarding the urinary excretion of siRNA, the RFU levels of spot urine samples collected over time were examined using Nanodrop ND-3300.

In Vivo and Ex Vivo Imaging

To examine the in vivo distribution of siRNA with and without complex formation with PIC nanocarrier, the IVIS 200 Imaging System (Xenogen, Calif.), which consists of a highly sensitive cooling CCD camera installed in a non-light-leaking tight sample chamber, was used. Fluorescence signal images and measurements were acquired and analyzed using the Living Image software (Xenogen). Female BALB-c mice at 6 weeks of age were anesthetized using 1-3% isoflurane (Abbott Laboratories, IL), and a Cy5-labeled siRNA/PIC nanocarrier (0.5 ml, 5 nmol siRNA content) or naked Cy5-labeled siRNA (0.5 ml, 5 nmol) was intraperitoneally injected. Each mouse was placed on a warmed stage in the camera chamber, and continuously exposed to 1-2% isoflurane to keep it sedative. After imaging the living mouse, the mouse was euthanized, desired tissue was extirpated, and ex vivo imaging was performed within 30 minutes.

Evaluation of Silencing Effect of MAPK1 siRNA/PIC Nanocarrier in Chronic Glomerulonephritis To evaluate the knockdown effect of MAPK1 siRNA/PIC nanocarrier in glomeruli in vivo, MRL/lpr mice were selected. The mice were randomly divided into four groups (n=6) as follows: a group treated with MAPK1 siRNA/PIC nanocarrier, a group treated with non-silencing control siRNA/PIC nanocarrier, a group treated with MAPK1 siRNA-incorporating HVJ-E, and a non-treated group. Twice-a-week intraperitoneal injection was started at 12 weeks of age, and each siRNA was administered at a dose of 2 nmol per week. At 17 weeks of age, urine samples were collected, and urinary albumin excretion was detected using urinalysis paper. Next, blood samples were collected, and tissue was extirpated from all mice. One of the two kidneys was finely shredded, and a glomerular fraction was separated by a commonly used sieving method. The other kidney was prepared to obtain frozen sections, which were fixed in Methyl Carnoy.

Quantitative Realtime PCR (Q-RT-PCR)

Total cellular RNA was isolated using the RNeasy® kit (Qiagen), and first-strand cDNA was synthesized using RNAseH+ reverse transcriptase and random primers (Qiagen). Next, duplicate real time PCR assay was performed using probes (Qiagen) labeled with FAM or Yakima Yellow dye. The expressions of the housekeeping gene Rn18s and the target genes (MAPK1 and TGF-β) was simultaneously quantified in the same well. Next, the expressions of the target genes were normalized versus the expression of Rn18s. PCR was performed using ABI PRISM 7000 (Applied Biosystems, CA); first activation was performed at 95° C. for 15 minutes, and this was followed by 45 cycles of elongation at 76° C. for 45 seconds, denaturation at 94° C. for 45 seconds, and annealing and elongation at 56° C. for 45 seconds. Relative quantitation was achieved using a limit cycle measurement and a standard curve. All PCR experiments were performed in triplicate.

Western Blot Analysis

Western blotting was performed using the phospho-ERK1/2 antibody (Cell Signaling Technology, Beverly, Mass.) and the pan-ERK1/2 antibody (Cell Signaling Technology) to evaluate the expressions of phosphorylated MAPK1/2(ERK1/2) and total MAPK1/2 protein, respectively. The anti-β actin antibody used was a product manufactured by Cell Signaling Technology. The glomerular fraction was solubilized in cytolytic buffer solution at room temperature for 30 minutes, and the protein concentration in the sample was measured using a DC protein assay (Bio-Rad, Hercules, Calif., USA). 20 μg of protein was mounted on each lane, and sodium dodecylsulfate-polyacrylamide gel electrophoresis (SDS-PAGE) was performed under non-reducing conditions. The bound antibody was detected using 1 μg/ml alkaline phosphatase-conjugated anti-mouse IgG (Promega, Madison, Wis., USA). A 5-bromo-4-chloro-3-indolyl phosphate/nitroblue tetrazolium (BCIP/NBT) tablet (Sigma Fast; Sigma Chemical Co., St. Louis, Mo., USA) was used as the substrate.

Immunohistochemistry

Tissue for frozen sections was embedded in OCT (Lab-Tek Products; Miles Laboratories, Naperville, Ill., USA) and instantaneously frozen with liquid nitrogen. Using the Vectastain elite ABC Kit (Vector Laboratories, Inc., Burlingame, Calif.) and the peroxidase substrate kit DAB (Vector Laboratories), the frozen sections were stained for MAPK-1/2, phospho-MAPK-1/2, PAI-1 (American diagnostica, Inc, Stamford, Conn.) and FN (BD Biosciences, CA). In quantitative analysis, in more than 20 glomeruli randomly selected from each section, DAB-positive area was calculated by densitometry using image analyzing software (Molecular Devices Corp., Downingtown, Pa.).

Histological Evaluation of Glomerular and Tubulointerstitial Lesions

To examine the histology of the kidney, 4 μm sections of paraffin-embedded tissue were stained using the periodic acid Schiff (PAS) reagent. Glomerular lesions were semi-quantitatively counted using glomerulosclerosis scores by blinded observers who examined at least 30 randomly selected glomeruli in each specimen (Tanaka, T., et al. 2005. Lab. Invest. 85:1292-1307; Raij, L., Azar, S., and Keane, W. 1984. Kidney Int. 26:137-143). Glomerulosclerosis was defined as adhesion formation with regional or extensive obstruction of loop-like capillaries as detected by PAS staining, and its ratings were classified as follows (0 to 4): 0, normal; 1, influential on 0% to 25% of glomeruli; 2, influential on 25% to 50%; 3, influential on 50% to 75%; and 4, influential on 75% to 100%. Tubular lesions were semi-quantitatively counted by blinded observers who examined at least 20 randomly selected visual fields of cortex in each specimen (Tanaka, T., et al. 2005. Lab. Invest. 85: 1292-1307; Pichler, R. H., et al. 1995. J. Am. Soc. Nephrol. 6: 1186-1196). Tubulointerstitial lesions were classified on the basis of tubulocellularity, basement membrane thickness, and ratio of cell infiltration, dilation, atrophy, slough formation or interstitial dilation (0 to 5) as follows: 0, no change; 1, <10% tubulointerstitial lesions; 2, 10% to 25%; 3, 25% to 50%; 4, 50% to 75%; and 5, 75% to 100%. Furthermore, glomerular lesions were analyzed by the ratio of the number of fully sclerotic glomeruli to the total number of glomeruli on each transversal cross section, and also analyzed by semi-quantitative determination of PAS-positive area in glomeruli using image analysis software.

In Situ Hybridization

To determine the sequences of the probes, databases were searched using Megablast (which optimizes sequences of higher homology), sequences 50 bases long that were complementary to mouse MAPK1 mRNA and TGF-β mRNA and lacked significant homology to other known sequences, were selected. 50 picomole of oligonucleotide probe was labeled using the DIG oligonucleotide tailing kit (Roche Diagnostics, Mannheim, Germany). Free DIG was removed by ethanol precipitation, and the probe was dissolved in diethyl pyrocarbonate-treated water. In situ hybridization was performed per a reported protocol (Miyazaki, M., et al. 1994. Intern. Med. 33:87-91; Yamada, K., et al. 2001. Kidney Int. 59: 137-146). In summary, a frozen section (4 μm thick) was fixed in 4% para-formaldehyde solution in PBS, deproteinized with HCl, and digested with proteinase K (Sigma Chemical Co.). The specimen was pre-hybridized in a prehybridization buffer solution, the buffer solution was discharged, and the specimen was hybridized with a digoxigenin (DIG)-labeled oligonucleotide probe in the prehybridization buffer solution overnight. After the hybridization, the DIG-labeled probe was visualized using a sheep polyclonal anti-DIG antibody (Roche Diagnostics, Mannheim, Germany), a horseradish peroxidase (HRP)-conjugated rabbit anti-sheep antibody (Dako) and an HRP-conjugated swine anti-rabbit antibody (Dako). Colors were developed using diaminobenzidine tetrahydrochloride (DAB Chromogen, Dako) and 0.03% $H_2O_2$ in 0.05 mol/L Tris-HCl, pH 7.6. The section was counterstained with Methyl Green (Vector Laboratories, Burlingame, Calif.). To evaluate the reaction specificity, a sense probe corresponding to the sequence was used in place of an antisense probe.

Measurement of Urinary Protein and Blood Urea Nitrogen

Urinary protein was detected using urinalysis paper and recorded semi-quantitatively at 0 to 3. Blood urea nitrogen (BUN) was measured by the urease-glutamate dehydrogenase method using UN-S (Denka Seiken, Tokyo, Japan).

Statistical Analyses

All values are expressed as mean+/−SE. Significant differences among the groups were tested using ANOVA. A P-value under 0.05 was judged to indicate statistical significance.

Results

Features of Polyion Complex Nanocarrier

Figure 1B:
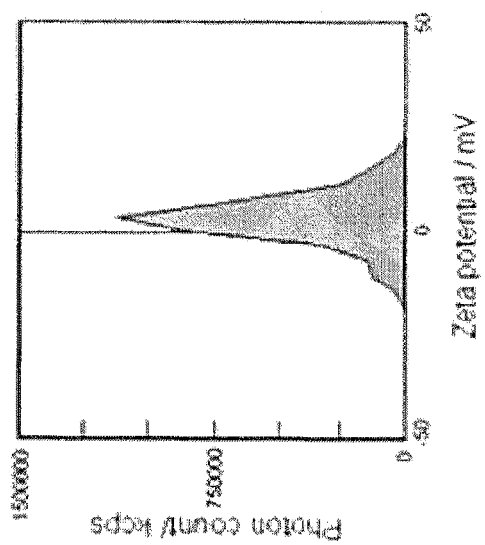
[FIG. 1B] Shown are histographic analyses of a polyion complex (PIC) nanocarrier. The distribution of the size of the PIC nanocarrier was determined by dynamic light scattering.
Figure 1B:
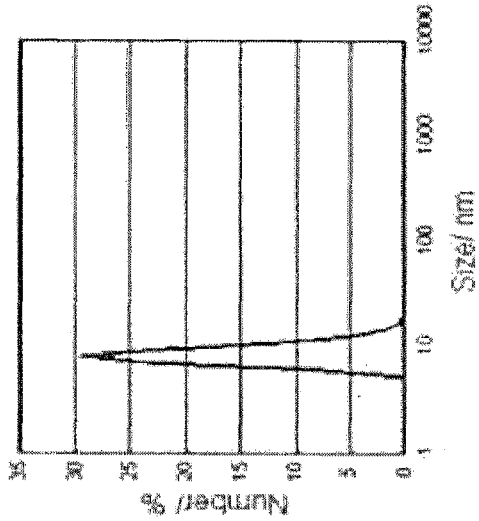
Figure 1B:
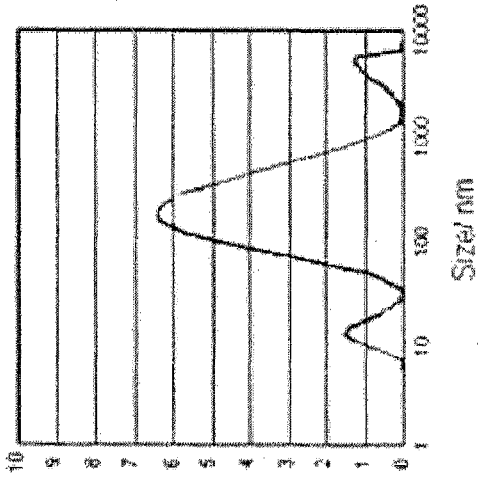
Figures 1C, 2A:
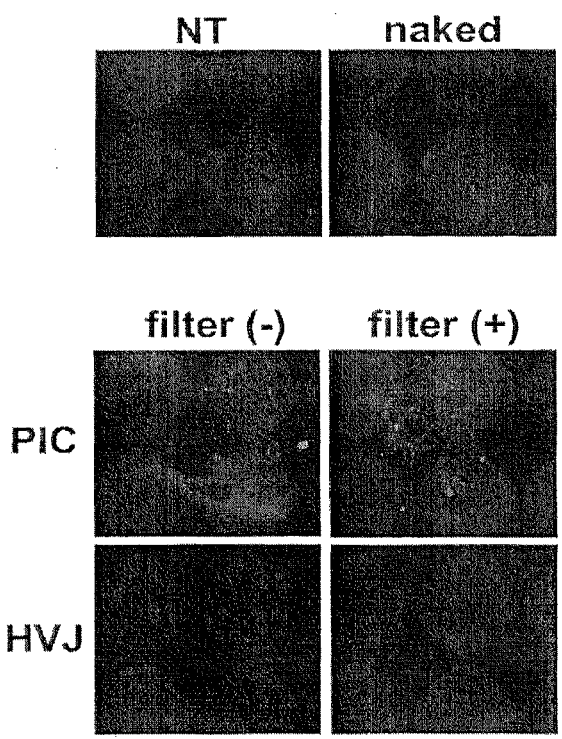
[FIG. 1C] Shown are the results obtained by mixing a Cy3-labeled siRNA and PEG-PLL in a ratio of N/P=0 to 2.8 in 10 mM Hepes (pH 7.3) buffer solution, and measuring the fluid dynamic diameter of the formed PIC nanocarrier by fluorescence correlation spectroscopy.
[FIG. 2A] Shown are fluorescence photomicrographs of cultured mesangial cells treated with FITC-labeled non-silencing control siRNA (naked), FITC-labeled siRNA/PIC nanocarrier (PIC), or FITC-labeled siRNA-incorporating HVJ-E(HVJ), or non-treated (NT) cells. It was shown that the PIC nanocarrier passed a filter having a 0.2 μm pore size, compared with HVJ-E. Representative results of three independent experiments are shown. (Original magnification; ×200)

In this study, a complex of siRNA and PIC nanocarrier was prepared by simply mixing a PEG-PLL copolymer (12-73) and an siRNA solution in a ratio of N/P=1.4 (FIG. 1A). A histographic analysis by dynamic light scattering (DLS) measurement demonstrated the formation of a complex of about 10 nm size (FIG. 1B). This was also confirmed by the fact that the size of the complex was measured to be 13.7±0.1 nm by fluorescence correlation spectroscopy (FCS) analysis (FIG. 1C). The nanocarrier is smaller than HVJ-E, which was measured to be 297.3 nm in diameter by DLS analysis. The diameter of the naked siRNA was shown by FCS analysis to be 6.56±0.07 nm (FIG. 1C). Therefore, the complex of the present invention can exist as a unit configured with the siRNA and a relatively smaller number of PEG-PLL copolymers.

In Vitro Transfection of Mesangial Cells with Complex of siRNA and Nanocarrier

Figure 2B:
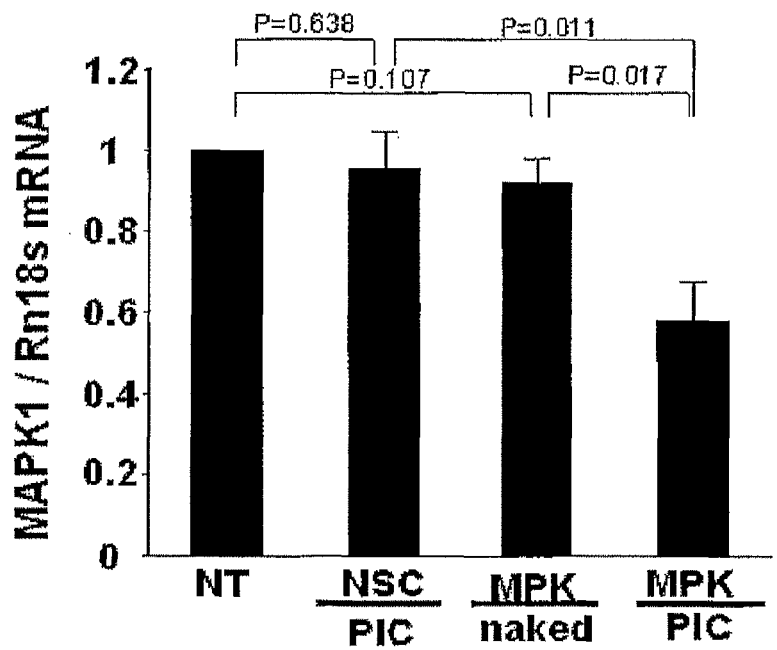
[FIG. 2B] Shown is Q-RT-PCR analysis of the expression of MAPK1 in mesangial cells transfected with MAPK1 siRNA/PIC nanocarrier in vitro. P-values were calculated by ANOVA. Mean+/−s.e., n=5. NT; no treatment, NSC/PIC; non-silencing control siRNA/PIC nanocarrier, MPK/naked; naked MAPK1 siRNA, MPK/PIC; MAPK1 siRNA/PIC nanocarrier.
Figure 2C:
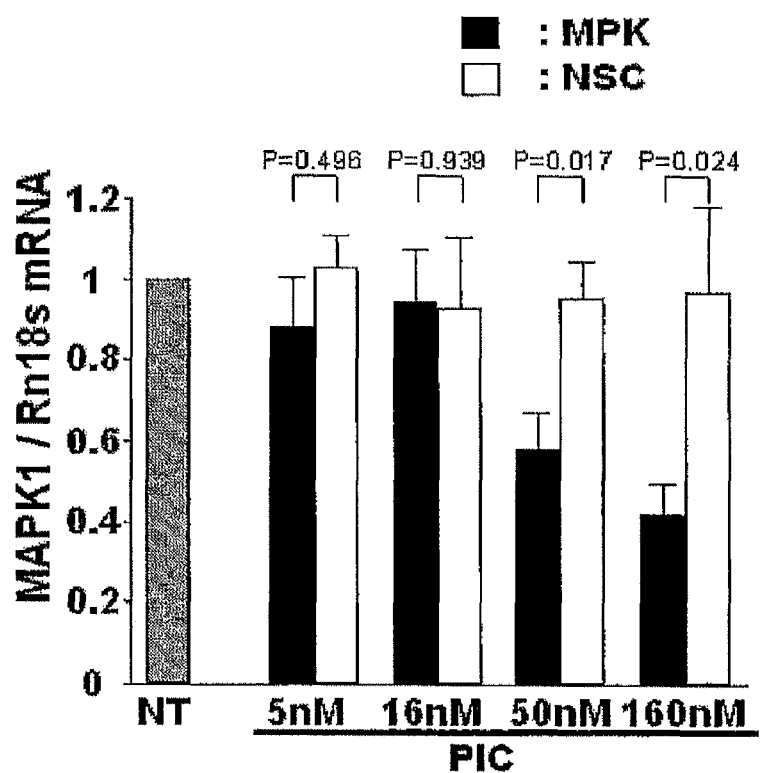
[FIG. 2C] Shown is Q-RT-PCR analysis of the expression of MAPK1 in mesangial cells transfected with MAPK1 siRNA/PIC nanocarrier in vitro. Transfection of the MAPK1 siRNA/PIC nanocarrier dose-dependently suppressed the expression of MAPK1 mRNA significantly at MAPK1 siRNA concentrations exceeding 50 nM. P-values were calculated by ANOVA. Mean+/−s.e., n=5. NT; no treatment.

To examine the transfection efficiency of the PIC nanocarrier in vitro, a complex of a fluorescein isothiocyanate (FITC)-labeled non-silencing control (NSC) siRNA and the PIC nanocarrier, FITC-labeled NSC siRNA incorporated in HVJ-E or FITC-labeled naked NSC siRNA was applied to cultured mouse mesangial cells. The cells treated with the siRNA/PIC nanocarrier emitted intense fluorescence (FIG. 2A), whereas the control cells or the cells treated with the naked siRNA were mostly negative. Furthermore, to mimic the size selection barrier by fenestrated glomerular endothelial cells, the sample was filtered through a filter of 0.2 μm pore size, after which it was transfected to mesangial cells. The fluorescence almost disappeared in the filter-pretreated siRNA/HVJ-E group, whereas the cells treated with the filtered siRNA/PIC nanocarrier retained high fluorescence intensity. This suggests that the siRNA/PIC nanocarrier is able to pass a filter of 0.2 μm size (FIG. 2A). Next, the gene silencing effect of the MAPK1 siRNA/PIC nanocarrier in mesangial cells was examined. Quantitative realtime (Q-RT) PCR analysis showed that the expression of MAPK1 mRNA was significantly suppressed by the MAPK1 siRNA at 50 nM or higher concentrations (FIGS. 2B and C).

In Vivo and Ex Vivo Optical Imaging Analysis

Figure 3:
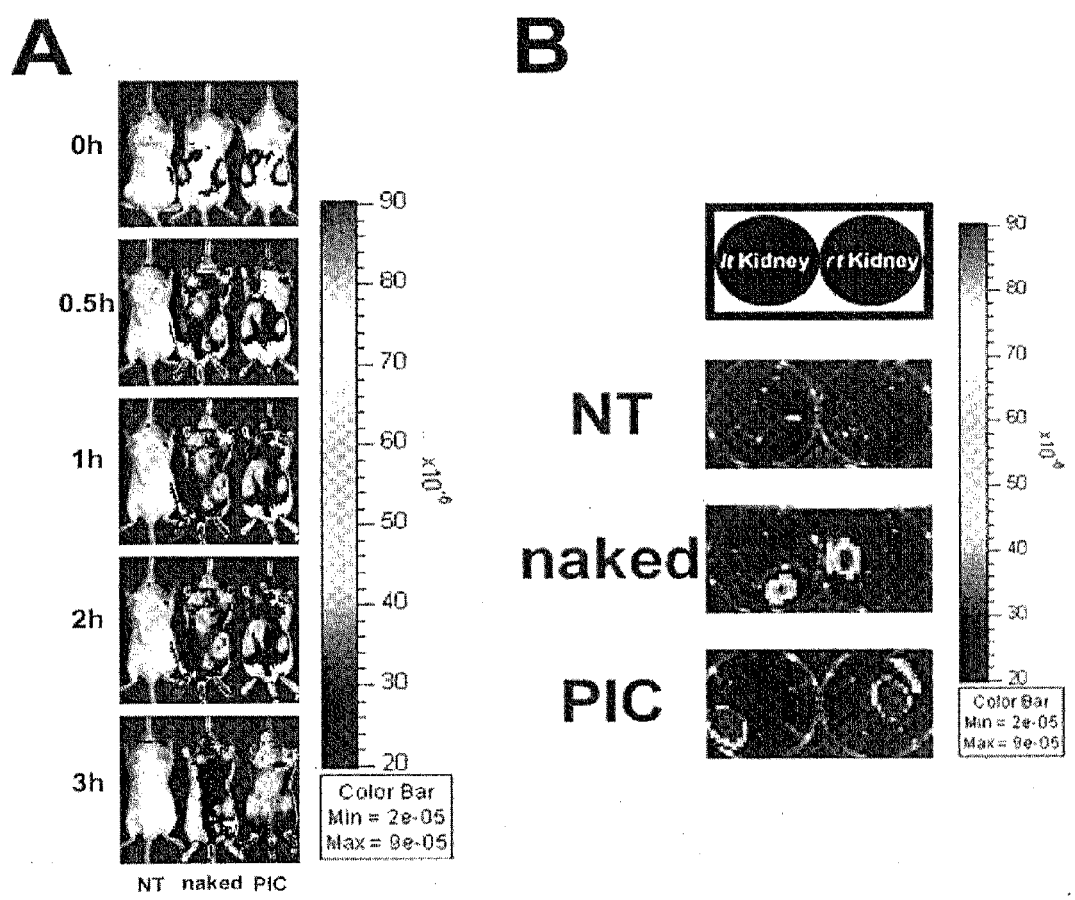
[FIG. 3] Shown are in vivo and ex vivo optical imaging analyses. (A) The Cy5-labeled control siRNA/PIC nanocarrier accumulated in the kidney soon after intraperitoneal injection, and retained a high fluorescence signal in the kidney beyond 3 hours. (B) Ex vivo imaging in the kidney at 3.5 hours after injection. Extended signals were detected in the entire kidney, including the cortical region, in mice treated with the siRNA/PIC nanocarrier, compared with the naked siRNA. Representative results of three independent experiments are shown. NT; no treatment, naked; naked siRNA, PIC; siRNA/PIC nanocarrier.

To examine the systemic distribution of siRNA-nanocarrier complex, an IVIS system was used. In whole body images of mice, intense fluorescence was shown in both kidneys just after intraperitoneal injection of 5 nmol of Cy5-labeled siRNA/PIC nanocarrier. The high fluorescence signal in the kidney could be significantly visualized for 3 hours, with the minimum contrast, compared with the naked siRNA (FIG. 3A). Furthermore, 3.5 hours after intraperitoneal administration of the naked siRNA or siRNA/PIC nanocarrier, ex vivo imaging analysis of major tissues was performed. Fluorescence signals were detected in the liver, lungs and kidneys in both groups of mice treated with the naked siRNA or siRNA/PIC nanocarrier, respectively. However, in the mice treated with the siRNA/PIC nanocarrier, the entire kidney exhibited higher fluorescence than in the case of the naked siRNA, which was distributed in the central region of the kidney. It is suggested that the siRNA/PIC nanocarrier is persistently distributed in the cortical region, where glomeruli are localized (FIG. 3B).

Intraglomerular Accumulation and Localization of Nanocarrier

Figure 4A:
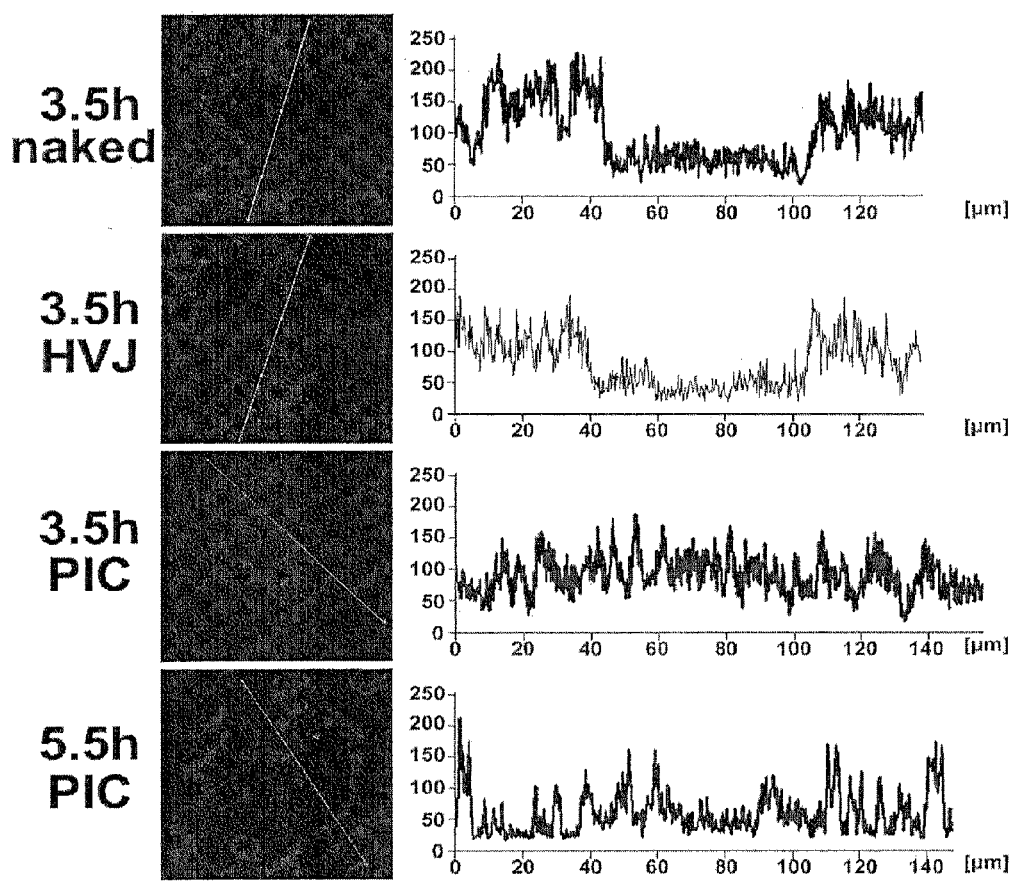
[FIG. 4A] Shown is intraglomerular accumulation of PIC nanocarrier. Confocal microscopic analysis and cross-sectional intensity measurement showing a Cy5-labeled siRNA/PIC nanocarrier incorporated in glomeruli at 3.5 hours or 5.5 hours after intraperitoneal injection. Naked; naked siRNA, PIC; siRNA/PIC nanocarrier, HVJ; siRNA-incorporating HVJ-E.
Figure 4B:
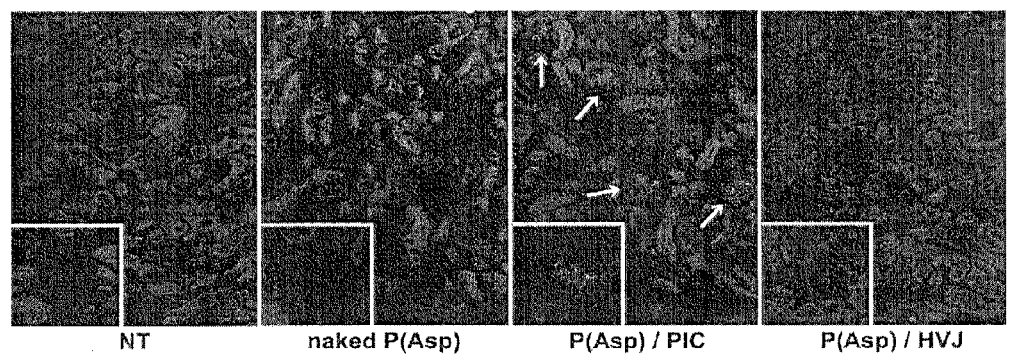
[FIG. 4B] Fluorescence photomicrographs showing intraglomerular accumulation of PIC nanocarrier. Fluorescence photomicrographs of kidney sections at 6 hours after intraperitoneal injection of an FITC-labeled poly($\alpha,\beta$-aspartic acid) [P(Asp)] PIC nanocarrier (P(Asp)/PIC), compared with no treatment (NT), naked P (Asp) and P (Asp)-incorporating HVJ-E (P(Asp)/HVJ). High fluorescence intensity was detected in almost all glomeruli of P(Asp)/PIC-treated mice (yellow arrows and insets). Autofluorescence was found in the tubular region. Representative results of three independent experiments are shown. (Original magnification; ×200)
Figure 10:
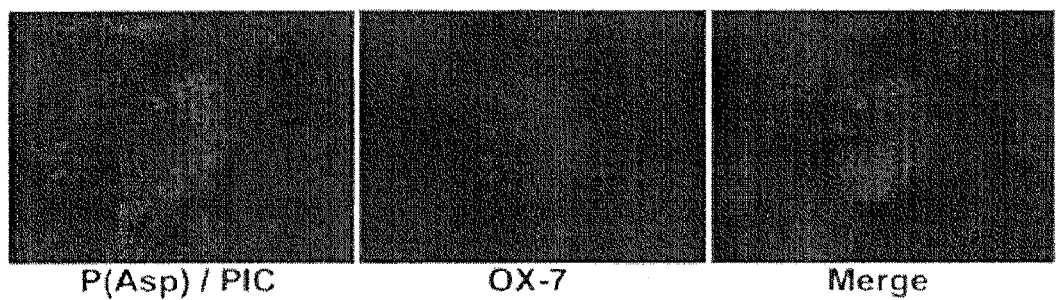
[FIG. 10] Shown is localization of PIC nanocarrier in glomeruli. In rat kidney specimens at 120 minutes after intraperitoneal injection of FITC-P(Asp)/PIC nanocarrier, the FITC-positive area of glomeruli was almost superposed by OX-7 staining (Rhodamine Red). This suggests that the PIC nanocarrier is incorporated mainly in the mesangial region. P(Asp)/PIC; FITC-labeled poly(α,β-aspartic acid)/PIC nanocarrier.

A Cy5-labeled siRNA/PIC nanocarrier, Cy5-labeled siRNA-incorporating HVJ-E or a Cy5-labeled naked siRNA was intraperitoneally injected; 3.5 and 5.5 hours later, using frozen sections of the kidney, the localization of siRNA in the kidney was examined under a confocal microscope. Cross-sectional analysis by fluorescence intensity profiling demonstrated higher signals in the glomeruli of the mice treated with the siRNA/PIC nanocarrier for 3.5 hours than in the mice treated with the naked siRNA or siRNA/HVJ-E (FIG. 4A). The autofluorescence in the tubular region was found in all groups. Using FITC-labeled poly(α,β-aspartic acid) [P(Asp)] in place of siRNA as a model of polyanion, the P(Asp)/PIC nanocarrier exhibited high fluorescence intensity in almost all glomeruli under a fluorescence microscope (FIG. 4B). To further examine the intracellular localization of the injected P(Asp)/PIC nanocarrier in glomeruli, staining with the mesangium marker OX-7 was performed in Wistar rats. The FITC-positive area in glomeruli generally overlapped OX-7 staining; it was suggested that the aforementioned complex was localized mainly in the mesangium (FIG. 10).

Persistence of Blood Circulation of Complex of siRNA and Nanocarrier

Figure 5A:
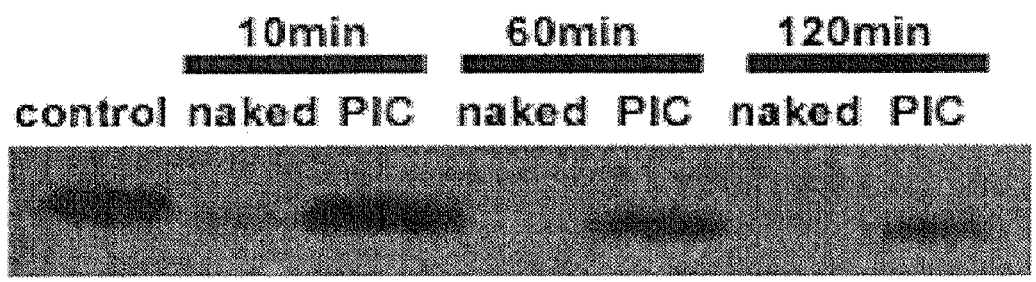
[FIG. 5A] A polyacrylamide gel image visualized by EtBr staining showing that an siRNA/PIC nanocarrier exhibits extended blood circulation compared with naked siRNA.
Figure 5B:
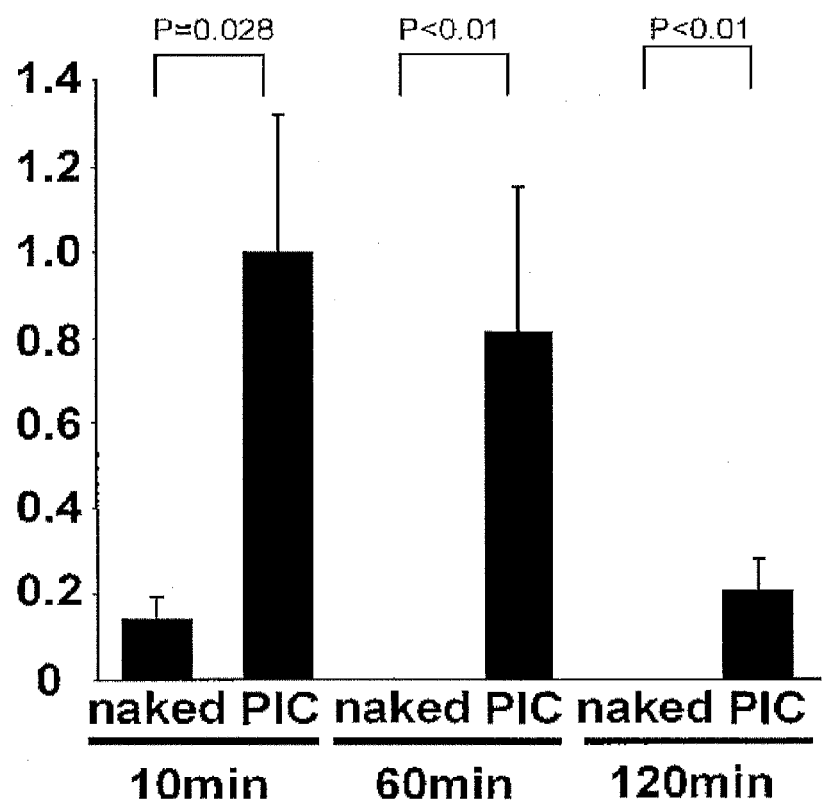
[FIG. 5B] Shown is a densitometric analysis of the polyacrylamide gel band visualized in FIG. 5A. P-values were calculated by ANOVA. Means+/−s.e., n=3.
Figure 5C:
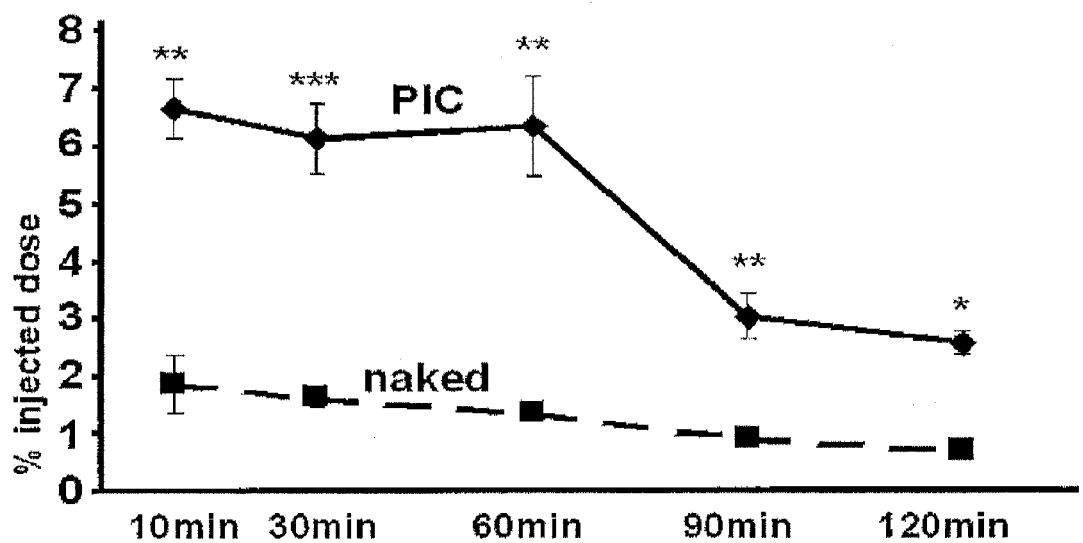
[FIG. 5C] Shown are the results of direct measurements of fluorescence intensity of siRNA/PIC nanocarrier and naked siRNA in mouse plasma over time. PIC; Alexa Fluor 647-labeled non-silencing control (NSC) siRNA/PIC nanocarrier, naked; naked Alexa Fluor 647-labeled NSC siRNA. The 100% injection dose was estimated using total blood volume based on mouse body weight. *P<0.05, <0.01, *<0.001 vs. naked siRNA, ANOVA, mean+/−s.e., n=4.
Figure 11:
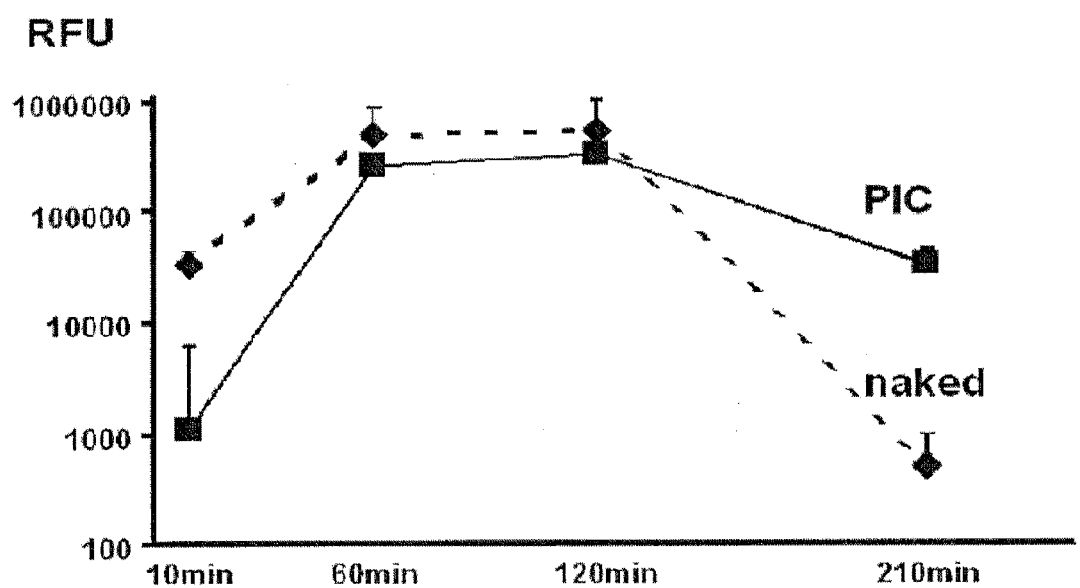
[FIG. 11] Shown is urinary excretion of siRNA/PIC nanocarrier. (A) Shown is the relative fluorescence intensity of urine sample spots after intraperitoneal injection of Alexa Fluor 647-labeled non-silencing control siRNA (naked) or Alexa Fluor 647-labeled siRNA/PIC nanocarrier at a dose of 5 nmol (siRNA content). The naked siRNA was rapidly excreted after injection, with only a trace amount of siRNA detected in the urine at 210 minutes, but the urinary excretion of the siRNA/PIC nanocarrier or metabolites thereof was delayed. (B) Shown are representative urine samples at various time points.
Figure 11:
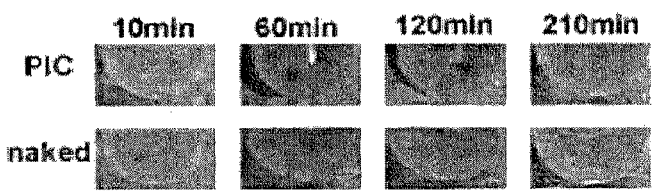

To evaluate the stability of the blood circulation of siRNA/PIC nanocarrier, the siRNA was subjected to polyacrylamide gel electrophoresis. Ethidium bromide (EtBr) staining demonstrated that an intraperitoneally injected naked siRNA was eliminated from the blood rapidly within 10 minutes, and that the siRNA/PIC nanocarrier extended the circulation of the siRNA by 2 hours after intraperitoneal injection (FIG. 5A, B). Also, after injection of Alexa Fluor 647-labeled siRNA/PIC nanocarrier or Alexa Fluor 647-labeled naked siRNA, fluorescence intensity in mouse plasma was directly measured over time (FIG. 5C). The Alexa Fluor 647-labeled siRNA/PIC nanocarrier was found to continue to exhibit fluorescence for 2 hours, compared with the naked siRNA. Regarding the urinary excretion of the siRNA, the fluorescence intensity of spot urine was measured. The naked siRNA was rapidly excreted after injection, with only a small amount of fluorescence detected in urine samples after 210 minutes, whereas the urinary excretion of the siRNA/PIC nanocarrier was delayed by about 60 minutes (FIG. 11A, B).

Figure 6A:
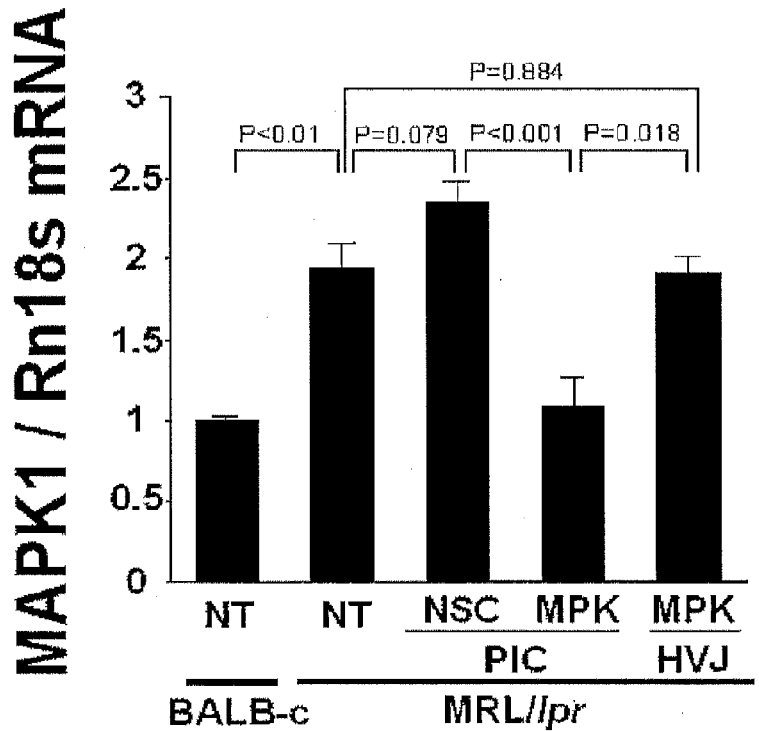
[FIG. 6A] Shown is MAPK1 silencing in glomeruli by MAPK1 siRNA/PIC nanocarrier. Q-RT-PCR analysis of the expression of MAPK1 mRNA in isolated glomeruli from MRL/lpr mice. NT; no treatment, NSC/PIC; non-silencing control siRNA/PIC nanocarrier, MPK/PIC; MAPK1 siRNA/PIC nanocarrier, MPK/HVJ; MAPK1 siRNA-incorporating HVJ-E. Non-treated BALB-c mice were used for control. P-values were calculated by ANOVA. Mean+/−s.e., n=5.
Figure 6B:
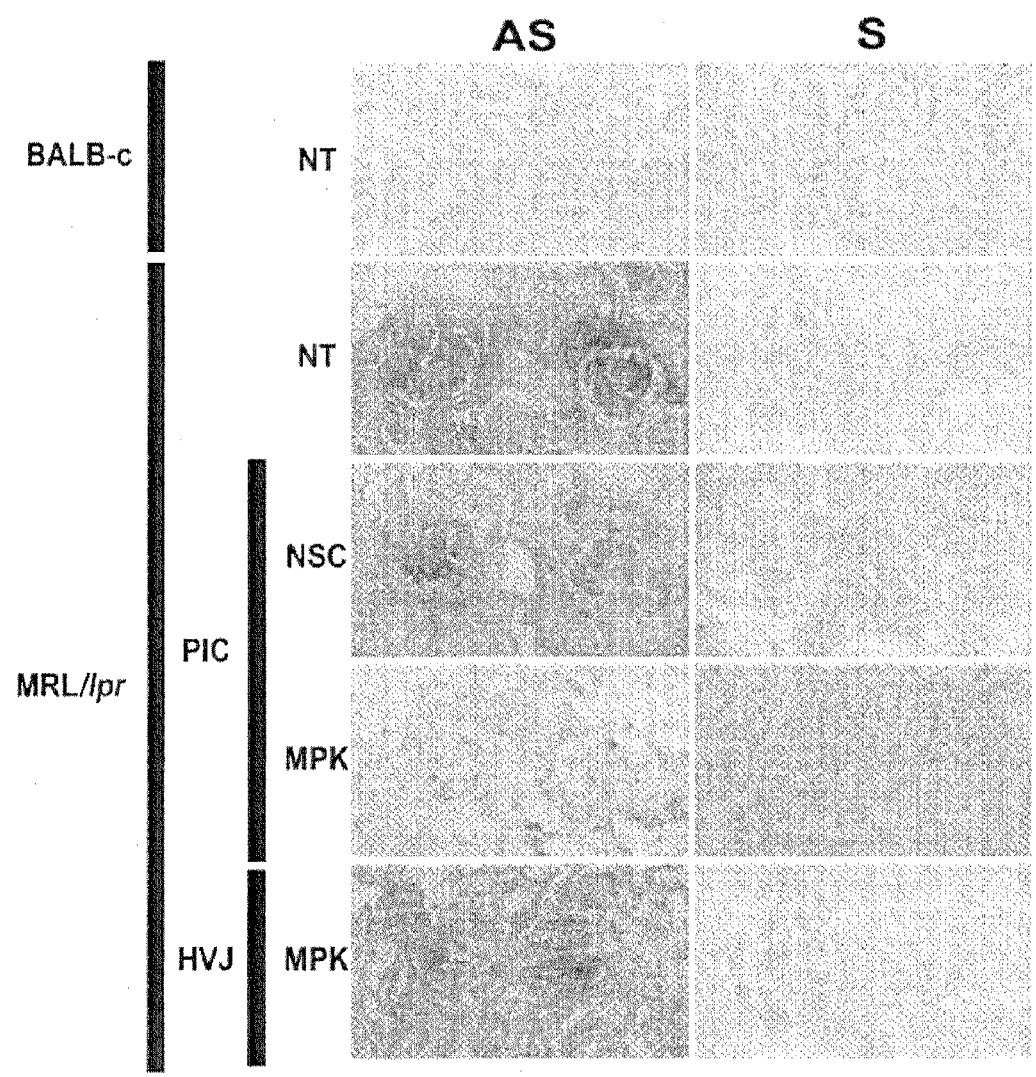
[FIG. 6B] Shown is in situ hybridization of kidney sections with MAPK1 mRNA using antisense (AS) and sense (S) probes. (Original magnification, ×200)
Figure 6C:
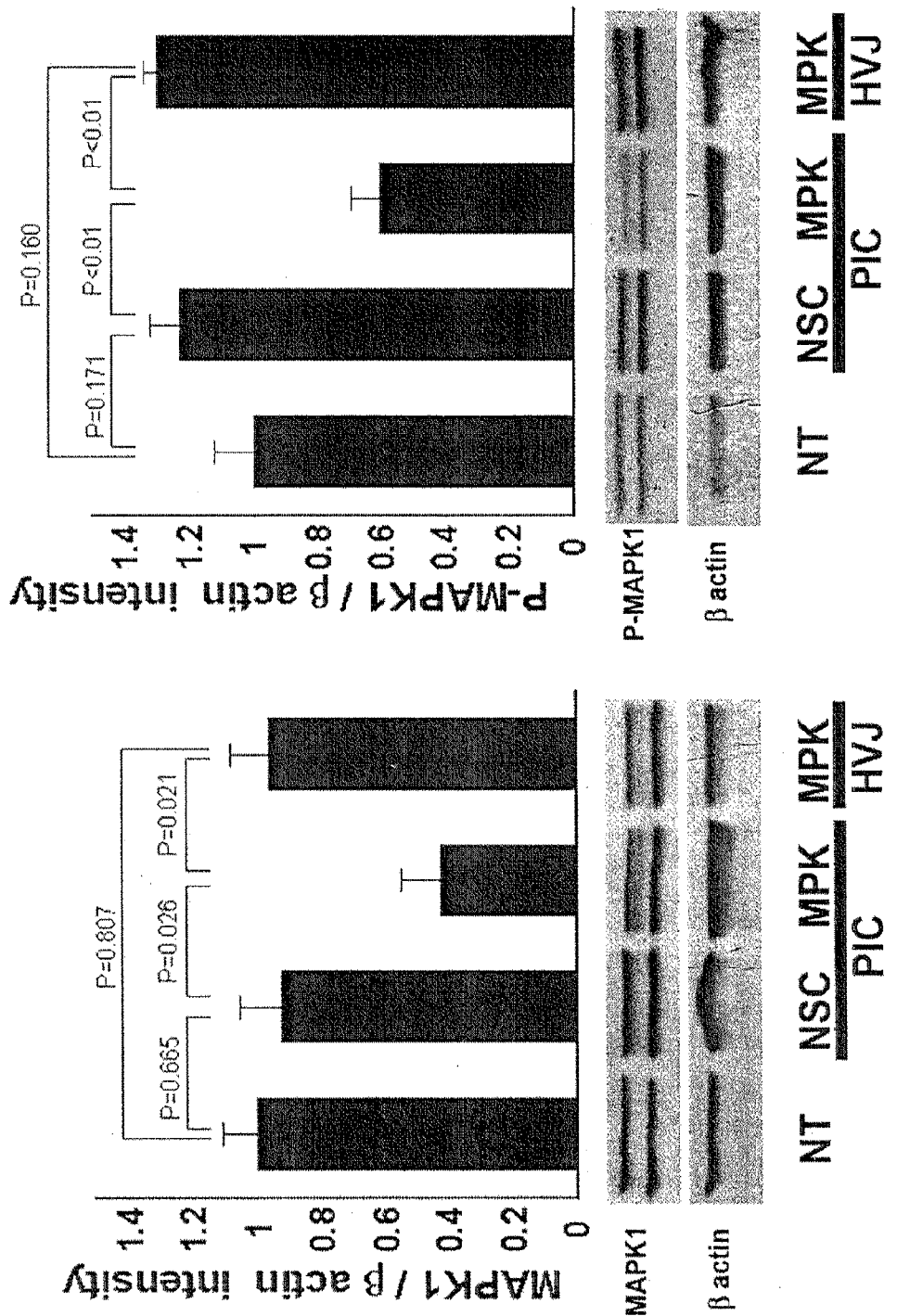
[FIG. 6C] Western blot showing MAPK1 silencing in glomeruli by MAPK1 siRNA/PIC nanocarrier and densitometric analysis of the results. The MAPK1 siRNA/PIC nanocarrier suppressed the expression of both MAPK1 protein (left) and P-MAPK1 protein (right). P-values were calculated by ANOVA. Mean+/−s.e., n=4.
Figure 6D:
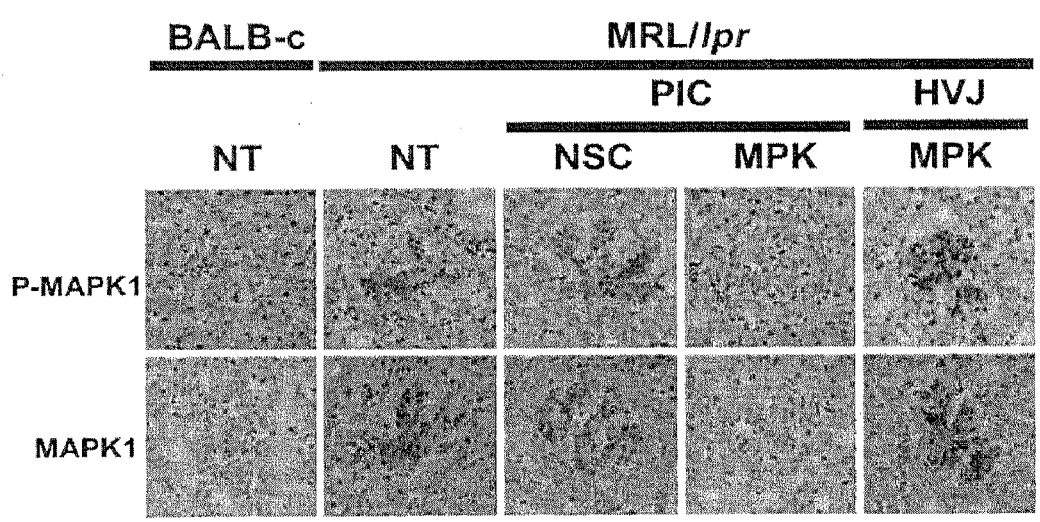
[FIG. 6D] Immunostaining of MAPK1 and P-MAPK1 in kidney sections showing MAPK1 silencing in glomeruli by MAPK1 siRNA/PIC nanocarrier. (Original magnification, ×200)
Figure 6E:
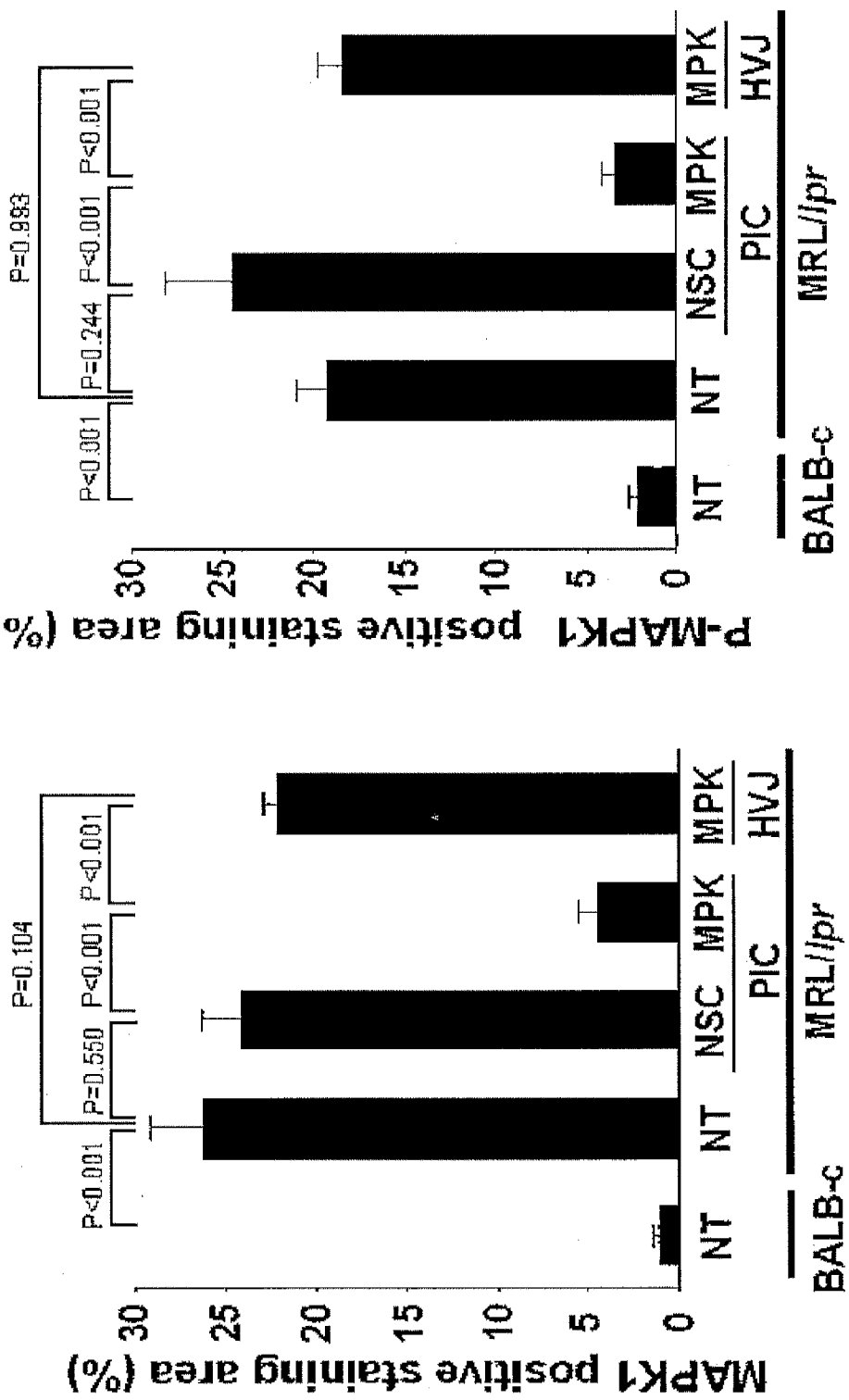
[FIG. 6E] Shown are the results of densitometric analysis in FIG. 6D. The data are expressed as area (%) positive for MAPK1 (left) or P-MAPK1 (right) staining in glomeruli.
Figure 7A:
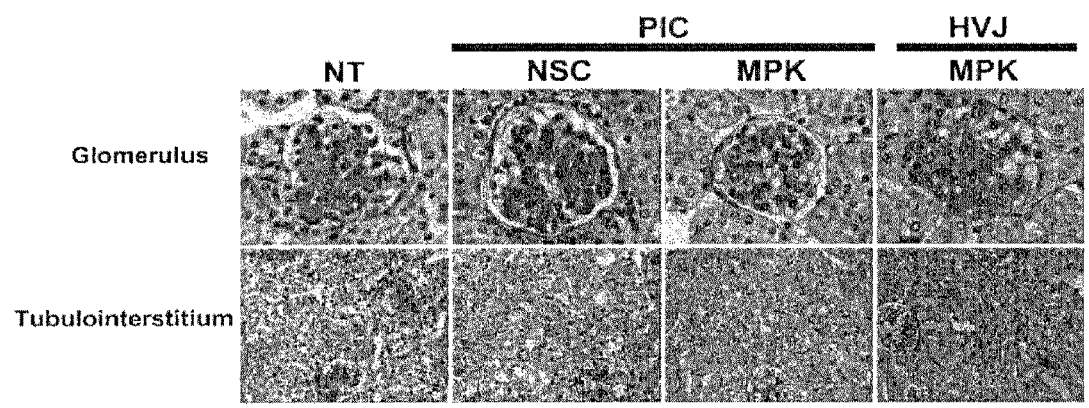
[FIG. 7A] Shown is amelioration of glomerular lesions by MAPK1 siRNA/PIC nanocarrier. Representative glomeruli (upper panel) and tubulointerstitial regions (lower panel) are shown. NT; no treatment, NSC/PIC; non-silencing control siRNA/PIC nanocarrier, MPK/PIC; MAPK1 siRNA/PIC nanocarrier, MPK/HVJ; MAPK1 siRNA-incorporating HVJ-E. (Original magnification, ×200)
Figure 7B:
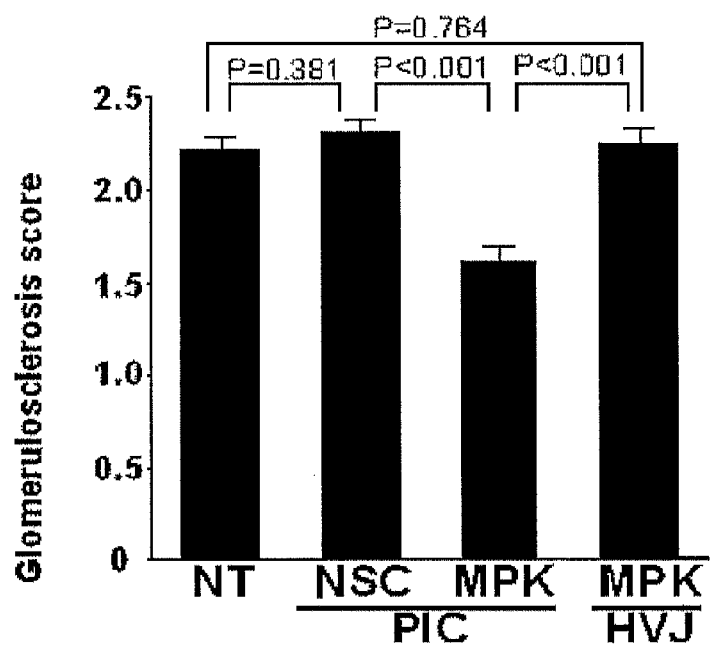
[FIG. 7B] A histological analysis of renal sections showing amelioration of glomerular lesions by MAPK1 siRNA/PIC nanocarrier. Glomerulosclerosis score significantly decreased in the group treated with MAPK1 siRNA/PIC nanocarrier. P-values were calculated by ANOVA. Mean+/−s.e., n=6.
Figure 7C:
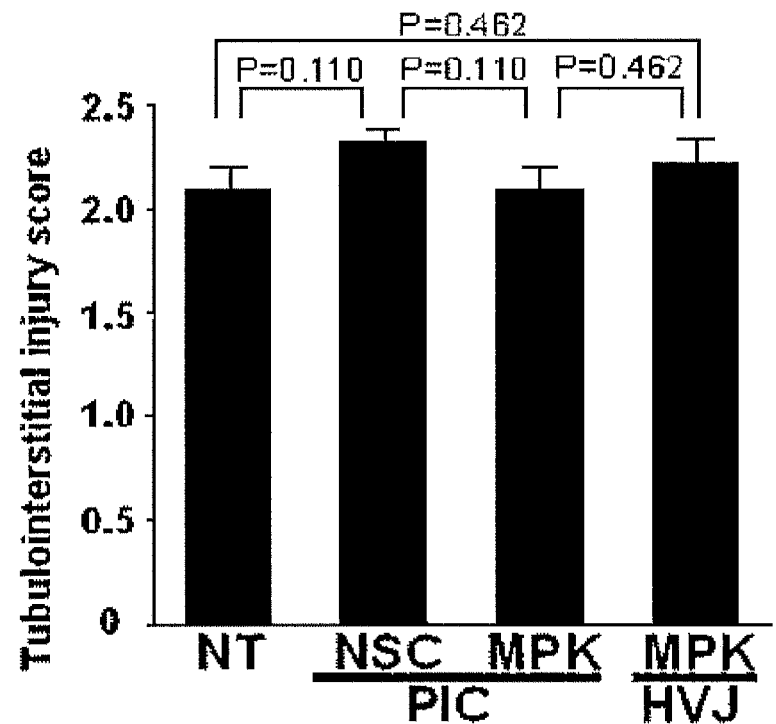
[FIG. 7C] A histological analysis of renal sections showing amelioration of glomerular lesions by MAPK1 siRNA/PIC nanocarrier. In semi-quantitative scoring of tubulointerstitial injury, there was no significant difference among the four groups. P-values were calculated by ANOVA. Mean+/−s.e., n=6.
Figure 7D:
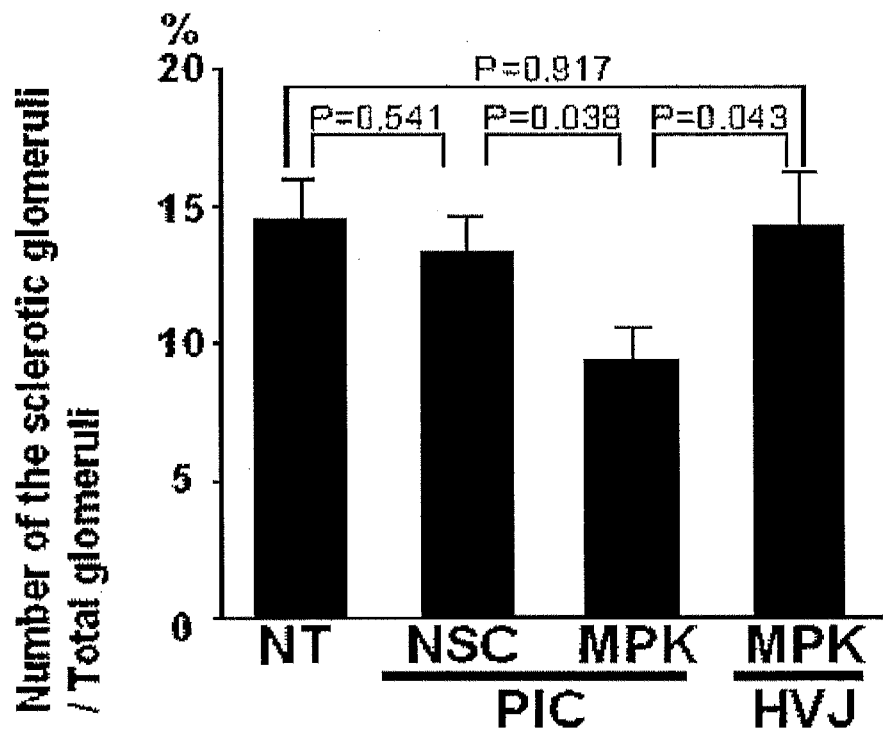
[FIG. 7D] A histological analysis of renal sections showing amelioration of glomerular lesions by MAPK1 siRNA/PIC nanocarrier. The number of fully sclerotic glomeruli decreased significantly in the group treated with MAPK1 siRNA/PIC nanocarrier. P-values were calculated by ANOVA. Mean+/−s.e., n=6.

MAPK1 Silencing in Glomeruli by MAPK1 siRNA/PIC Nanocarrier in Glomerulonephritis Mice To determine whether the MAPK1 siRNA/PIC nanocarrier has a gene silencing effect in glomeruli in a living organism, lupus nephritis model MRL/lpr mice were used. After intraperitoneal injection of the MAPK1 siRNA/PIC nanocarrier, a control siRNA/PIC nanocarrier or MAPK1 siRNA-incorporating HVJ-E was repeated twice a week between 12 and 16 weeks of age, mice at 17 weeks of age were subjected to experiments. Q-RT-PCR analysis revealed that the expression of MAPK1 mRNA in isolated glomeruli was significantly suppressed in the mice treated with the MAPK1 siRNA/PIC nanocarrier, but the control siRNA/PIC nanocarrier or MAPK1 siRNA-incorporating HVJ-E was ineffective (FIG. 6A). To obtain direct evidence for MAPK1 silencing in glomeruli by the MAPK1 siRNA/PIC nanocarrier, in situ hybridization of MAPK1 mRNA was performed using kidney sections. The expression of MAPK1 mRNA was almost completely inhibited in the glomeruli of the mice treated with the MAPK1 siRNA/PIC nanocarrier, compared with control siRNA/PIC nanocarrier or non-treated samples (FIG. 6B). Western blot analysis of sieved glomerular fractions demonstrated that total MAPK1 and phosphorylated MAPK1 protein levels decreased in the mice treated with the MAPK1 siRNA/PIC nanocarrier (FIG. 6C). Immunohistochemical analysis showed that in the MAPK1 siRNA/PIC nanocarrier group, both MAPK1 and phosphorylated MAPK1 were almost completely suppressed in glomeruli, compared with the control siRNA/PIC nanocarrier or the non-treated group (FIGS. 6D and E). Treatment with MAPK1 siRNA-incorporating HVJ-E did not suppress the expression of MAPK1 mRNA and MAPK1 protein in glomeruli (FIG. 6A to E).

siRNA-mediated Intraglomerular MAPK1 Silencing by Nanocarrier Improves Glomerular Histology and Laboratory Values in Glomerulonephritis Mice Control MRL/lpr mice exhibited elevated BUN at 17 weeks of age, which agreed with a previous report (Prez de Lema, G., et al. 2001. J. Am. Soc. Nephrol. 12: 1369-1382). After MAPK1 siRNA/PIC nanocarrier was repeatedly intraperitoneally injected between 12 and 16 weeks of age, BUN and proteinuria levels decreased significantly compared with no treatment, control siRNA/PIC nanocarrier, or MAPK1 siRNA-incorporating HVJ-E (Table 1). Histopathological analysis of the kidney was performed by periodic acid Schiff (PAS) staining (FIG. 7A to E). Glomerulosclerosis score (FIG. 7B), the number of fully sclerotic glomeruli (FIG. 7D), and PAS-positive glomerular lesions (FIG. 7E) all decreased significantly in the group treated with MAPK1 siRNA/PIC nanocarrier. Meanwhile, tubulointerstitial lesions were not changed among the above-described groups (FIG. 7C).

Regulation of TGF-β Signaling Pathway by Intraglomerular MAPK1 Silencing

Figure 8A:
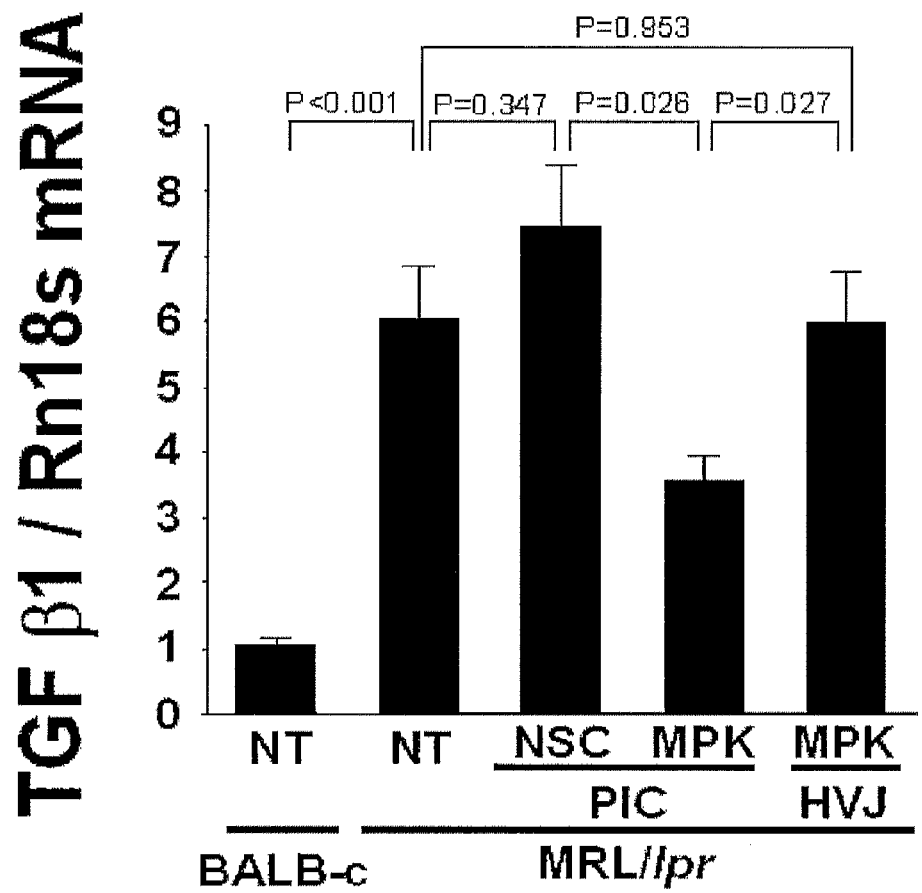
[FIG. 8A] Shown is suppression of the expression of TGF-β1 by MAPK1 silencing in glomeruli. Q-RT-PCR analysis revealed that treatment with MAPK1 siRNA/PIC nanocarrier suppressed the expression of TGF-β1 mRNA in glomeruli of MRL/lpr mice. NT; no treatment, NSC/PIC; non-silencing control siRNA/PIC nanocarrier, MPK/PIC; MAPK1 siRNA/PIC nanocarrier, MPK/HVJ; MAPK1 siRNA-incorporating HVJ-E. Non-treated BALB-c mice were used for control. P-values were calculated by ANOVA. Mean+/−s.e., n=5.
Figure 8B:
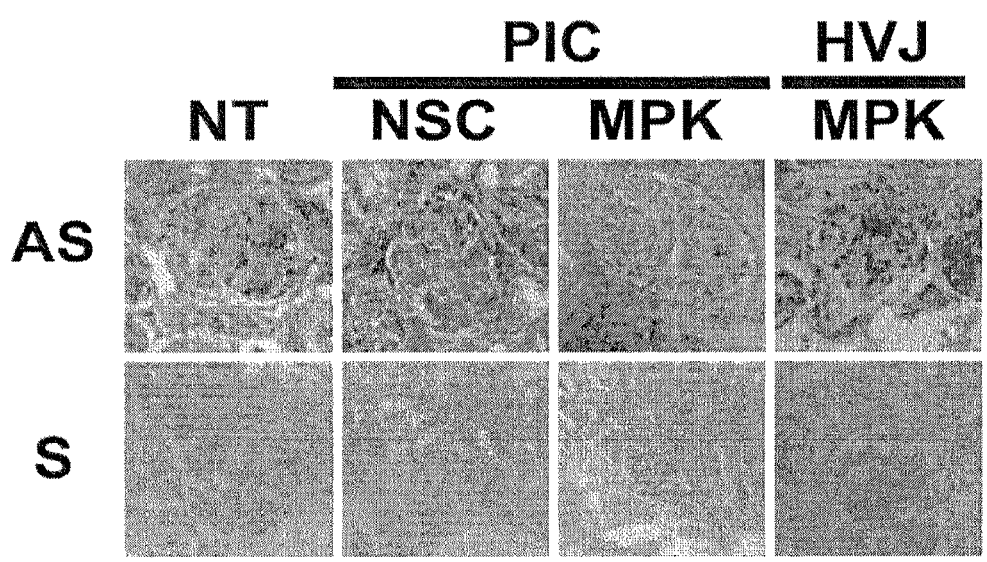
[FIG. 8B] Shown is suppression of the expression of TGF-β1 by MAPK1 silencing in glomeruli. Shown are the results of in situ hybridization of TGF-β1 mRNA in renal sections. AS; antisense probe, S; sense probe. (Original magnification, ×200)
Figure 9A:
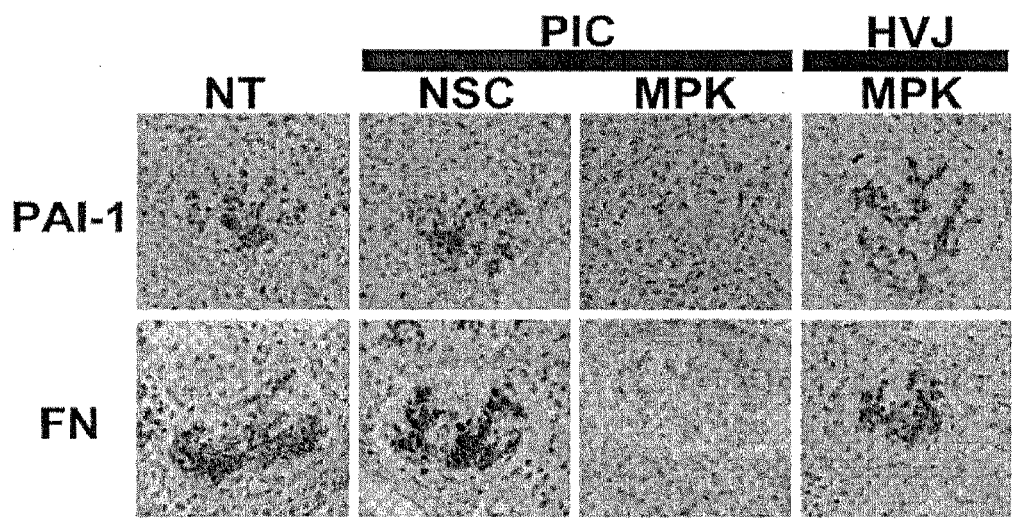
[FIG. 9A] Shown is immunostaining of plasminogen activation factor inhibitor 1 (PAI-1) and fibronectin (FN). The reductions in the expression of PAI-1 and FN in glomeruli were remarkable in the group treated with MAPK1 siRNA/PIC nanocarrier. NT; no treatment, NSC/PIC; non-silencing control siRNA/PIC nanocarrier, MPK/PIC; MAPK1 siRNA/PIC nanocarrier, MPK/HVJ; MAPK1 siRNA-incorporating HVJ-E. (Original magnification, ×200)
Figure 9B:
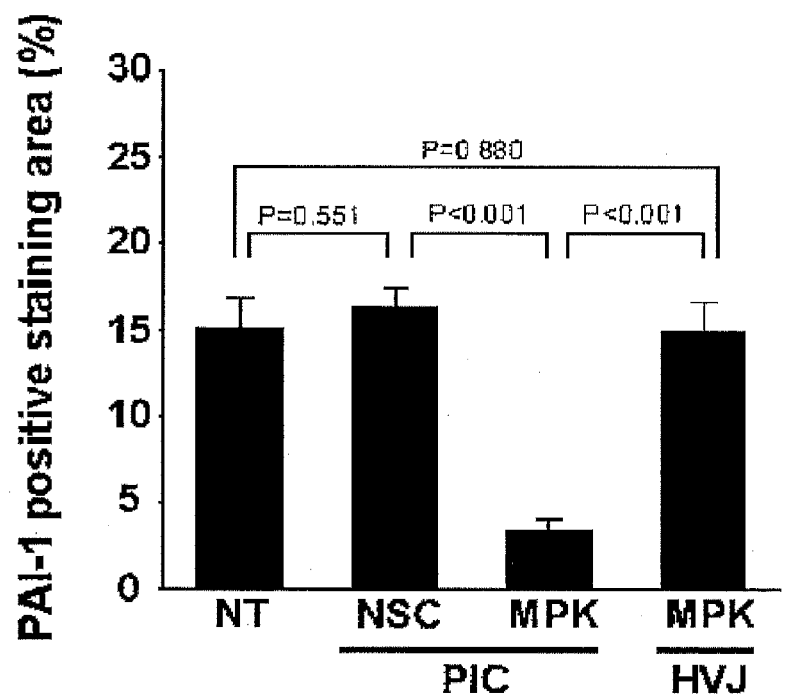
[FIG. 9B] Shown is densitometric analysis of PAI-1 staining of glomeruli in FIG. 9A. The data are expressed as area (%) positive for PAI-1 staining in each group of glomeruli. P-values were calculated by ANOVA. Mean+/−s.e., n=3.
Figure 9C:
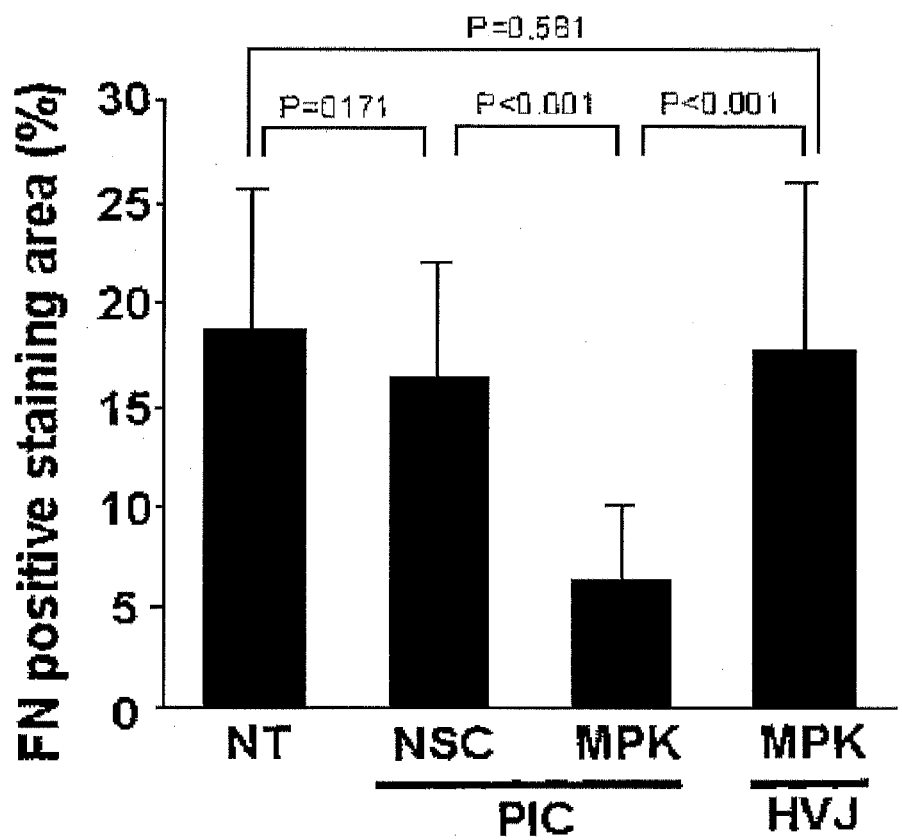
[FIG. 9C] Shown is densitometric analysis of FN staining of glomeruli in FIG. 9A. The data are expressed as area (%) positive for FN staining in each group of glomeruli. P-values were calculated by ANOVA. Mean+/−s.e., n=3.

Examined was the mechanism by which siRNA-mediated intraglomerular MAPK1 silencing by nanocarriers ameliorates glomerulosclerosis in progressive renal diseases. Q-RT-PCR analysis of isolated glomeruli showed that the expression of TGF-β1 mRNA was significantly suppressed in the group treated with MAPK1 siRNA/PIC nanocarrier (FIG. 8A). It was also shown by in situ hybridization that the expression of TGF-β1 mRNA was significantly inhibited in glomeruli of mice treated with the MAPK1 siRNA/PIC nanocarrier (FIG. 8B). Therefore, a role of MAPK1 as a regulatory factor upstream of TGF-β signaling is suggested. Finally, immunohistochemical analysis was performed on extracellular matrix protein and plasminogen activation factor inhibitor 1 (PAI-1), showing that the expression of the protein decreased definitely in the MAPK1 siRNA/PIC nanocarrier group (FIG. 9A to C). These results suggest the possibility that in the mouse model of lupus nephritis, increased MAPK1 stimulates the expression of TGF-β, which in turn leads to the accumulation of extracellular matrix protein and glomerulosclerosis.

TABLE 1

|  | NT | NSC/PIC | MPK/PIC | MPK/HVJ | P* | P** |
|---|---|---|---|---|---|---|
| Body weight (g) | 33.28 ± 6.115 | 34.66 ± 2.074 | 36.20 ± 2.078 | 30.31 ± 7.700 | 0.291 | 0.228 |
| Spleen (g) | 0.45 ± 0.149 | 0.59 ± 0.210 | 0.52 ± 0.185 | 0.52 ± 0.155 | 0.427 | 0.511 |
| Kidney (g) | 0.21 ± 0.039 | 0.22 ± 0.022 | 0.22 ± 0.018 | 0.23 ± 0.059 | 0.357 | 0.518 |
| BUN (mg/dl) | 29.66 ± 2.171 | 26.90 ± 4.057 | 19.18 ± 1.199 | 24.77 ± 1.350 | <0.001 | <0.01 |
| Urinary protein | 1.59 ± 0.775 | 1.55 ± 0.986 | 0.25 ± 0.274 | 1.50 ± 0.577 | <0.01 | <0.01 |

For urinary protein, semi-quantitative data obtained by urinalysis paper analysis are shown.

P* indicates a statistical significance level for NT group versus MPK/PIC group.

P** indicates a statistical significance level for NSC/PIC group versus MPK/PIC group.

In this study, efficient delivery of siRNA to glomeruli was successful using a delivery vehicle based on PEG-PLL copolymer. It was shown that using this system, a glomerulus-targeted MAPK1 siRNA suppresses the expression of MAPK1 at the mRNA and protein levels in glomeruli and ameliorates pathologic changes in glomerular disease in MRL/lpr mice.

The predominance of this system first of all, may consist in the size of the nanocarrier carrying the siRNA. As shown by dynamic light scattering measurements and fluorescence correlation spectroscopy analysis, the polyion complex (PIC) nanocarrier is much smaller than liposomes or HVJ-envelope vectors in conventional use (10-20 nm versus 200-500 nm) (FIGS. 1B and C). The nanocarrier in the present invention can permeate through capillary walls across the endothelial fenestrations about 100 nm, while escaping from passing through the glomerular basement membrane (GBM), which has a 4 nm pore size similar to the size of the albumin molecule and causes size-selective filtration barrier. Therefore, the nanocarrier comes in contact with mesangial cells because the mesangium adjoins directly with endothelial cells without intervening GBM (Kriz, W., Elger, M., Lemley, K., and Sakai, T. 1990. Kidney Int. 38 (Suppl. 30): S2-S9). In fact, accumulation of the PIC nanocarrier in glomeruli, particularly in mesangium, was clearly shown under a confocal microscope or fluorescence microscope (FIGS. 4A and B). Generally, since it is recommended that initial treatment of glomerular disease be performed before an irreversible pathologic change with endothelial disorder occurs in glomeruli, the nanocarrier in the present invention is thought to be clinically advantageous over liposomes, which are too large to pass undamaged endothelium (Imai, E., Takabatake, Y., Mizui, M., and Isaka, Y. 2004. Kidney Int. 65:1551-1555; Zhang, Y., et al. 2006. J. Am. Soc. Nephrol. 17:1090-1101; Isaka, Y., et al. 1993. J. Clin. Invest. 92:2597-2601; Maeshima, Y., et al. 1998. J. Clin. Invest. 101:2589-2597; Tomita, N., et al. 2000. J. Am. Soc. Nephrol. 11:1244-1252; Tuffin, G., Waelti, E., Huwyler, J., Hammer, C., and Marti, H. P. 2005. J. Am. Soc. Nephrol. 16:3295-3305). Because any conjugated siRNA (mostly bound to albumin) also gets filtered through damaged GBM, it is also undesirable for the treatment of renal diseases. Secondly, the extended circulating time of the nanocarrier in the present invention is important. The water solubility, enzyme tolerability, and remarkable biocompatibility, including the minimized nonspecific interaction with plasma protein and blood cells, are largely dependent on the PEG segment (Harada-Shiba, M., et al. 2002. Gene Ther. 9:407-414; Itaka, K., et al. 2003. Biomaterials. 24: 4495-4506; Harada, A., Togawa, H., and Kataoka, K. 2001. Eur. J. Pharm. Sci. 13:35-42; Akagi, D., et al. 2007. Gene Ther. 14:1029-1038). As demonstrated by polyacrylamide gel electrophoresis (FIGS. 5A and B) and fluorescence intensity measurement (FIG. 5C) of mouse plasma, the siRNA/PIC nanocarrier has extended circulating time compared with naked siRNA. Longevity in the circulation should be contributory to efficient accumulation in glomeruli. Thirdly, an advantage of the nanocarrier in the present invention as a pharmaceutical is the ease of preparation. The PLL segment is capable of forming a polyion complex with siRNA via an electrostatic interaction when simply mixed in a buffer solution (DeRouchey, J., et al. 2008. Biomacromolecules. 9:724-732). Furthermore, the PEG-PLL-based construct in this system is thought to be safer in clinical use than viral vectors (Wang, X., Skelley, L., Cade, R., and Sun, Z. 2006. Gene Ther. 13:1097-1103). PLL has been approved as a generally-recognized-as-safe (GRAS) substance by The Food and Drug Administration (FDA), and PEG has also been approved by FDA and is already used in sustained-action pharmaceuticals such as pegylated interferons. All these characteristics of nanocarriers are believed to allow pharmaceuticals for the treatment of glomerular diseases to be applied clinically.

The MRL/lpr strain is a mouse model of human systemic lupus erythematosus (SLE) caused by a mutation of the fas gene, to which encodes Fast, a member of the TNF-α receptor gene family that mediates apoptosis signals (Watanabe-Fukunaga, R., Brannan, C. I., Copeland, N. G., Jenkins, N. A., and Nagata, S. 1992. Nature. 356:314-317). In MRL/lpr mice, an autoimmune syndrome characterized by elevated levels of immunoglobulins (various autoantibodies) develops spontaneously, and nephritis and vasculitis with massive lymph proliferation occur (Theofilopoulos, A. N., and Dixon, F. J. 1985. Adv. Immunol. 37: 269-390; Cohen, P. L., and Eisenberg, R. A. 1991. Annu. Rev. Immunol. 9: 243-269). It is known that renal signs in MRL/lpr mice are mesangial proliferative glomerulonephritis at the beginning of the disease and diffuse proliferative glomerulonephritis with crescent formation in the last stage of course, and that the animal finally dies of irreversible progressed renal insufficiency (Andrews, B. S., et al. 1978. J. Exp. Med. 1148: 1198-1215). Therefore, treatment between 12 and 16 weeks of age enabled an evaluation of this nanocarrier system for its performance against pathological changes in the progression stage of glomerulonephritis.

Mitogen activation protein kinase (MAPK), a major intracellular signaling factor, has a wide variety of functions to regulate cell proliferation and apoptosis in inflammatory processes, including renal diseases (Herlaar, E., and Brown, Z. 1999. Mol. Medicine. Today. 5:439-447; Tian, W., Zhang, Z., and Cohen, D. M. 2000. Am. J. Physiol. Renal Physiol. 279: F593-F604). Recent studies have shown that activation of MAPK1, c-Jun $NH_2$ terminal kinase (JNK) and p38MAPK may be involved in glomerular injuries in experimental nephrosis (Bokemeyer, D., et al. 2000. J. Am. Soc. Nephrol. 11: 232-240; Bokemeyer, D., et al. 1997. J. Clin. Invest. 100: 582-588). It has been reported that in MRL/lpr mice, activation of p38MAPK is contributory to the pathogenicity of renal autoimmune diseases (Iwata, Y., et al. 2003. J. Am. Soc. Nephrol. 14:57-67). In this study, upregulation of MAPK1 was found in MRL/lpr mice. Definitely, MAPK1 silencing by MAPK1 siRNA/PIC nanocarrier in glomeruli (clearly demonstrated by in situ hybridization and immunohistochemistry (FIGS. 6B and D)) led to histological amelioration of glomerular lesions (FIG. 7A to E) and amelioration of renal function and urinary protein (Table 1).

In progressive renal diseases, TGF-β plays important roles as a fibrosis promoting factor in mesangial cells: 1) accentuates the production of collagen and fibronectin, 2) suppresses the expression of proteases that decompose extracellular matrix (ECM), and 3) stimulates the synthesis of ECM protease inhibitors such as plasminogen activation factor inhibitor 1 (PAI-1). Interestingly, it was found that while the intracellular signaling of the TGF-β superfamily is mediated by a series of Smad proteins (Huwiler, A., and Pfeilschifter, J. 1994. FEBS Lett. 354:255-258; Hartsough, M. T., and Mulder, K. M. 1995. J. Biol. Chem. 270:7117-7124; Frey, R. S., and Mulder, K. M. 1997. Cancer Res. 57: 628-633), the signaling pathway of MAPK is also involved in the signaling cascade of TGF-β in a wide variety of types of cells. MAPK1 and JNK were shown to get activated by TGF-β1 in mesangial cells (Huwiler, A., and Pfeilschifter, J. 1994. FEBS Lett. 354: 255-258; Hayashida, T., Decaestecker, M., and Schnaper, H. W. 2003. FASEB J. 17: 1576-1578). Furthermore, as the MAPK1 pathway, not JNK, was blocked, the TGF-β1-induced expression of ECM components decreased (Uchiyama-Tanaka, Y., et al. 2001. Kidney Int. 60:2153-2163). These in vitro findings suggest a synergistic role between TGF-β1-stimulated MAPK1 and Smad signaling, but no interaction in such a signaling cascade in vivo has been determined so far. On the other hand, while MAPK1 is known to mediate or precede the expression of TGF-β1 stimulated by various factors, including angiotensin II (Uchiyama-Tanaka, Y., et al. 2001. Kidney Int. 60: 2153-2163), rennin (Huang, Y., Noble, N. A., Zhang, J., Xu, C., and Border, W. A. 2007. Kidney Int. 72:45-52), mechanical expansion (Ingram, A. J., Ly, H., Thai, K., Kang, M., and Scholey, J. W. 1999. Kidney Int. 55:476-485; Ishida, T., Haneda, M., Maeda, S., Koya, D., and Kikkawa, R. 1999. Diabetes. 48: 595-602) and high glucose (Isono, M., Cruz, M. C., Chen, S., Hong, S. W., and Ziyadeh, F. N. 2000. J. Am. Soc. Nephrol. 11: 2222-2230; Hayashida, T., and Schnaper, H. W. 2004. J. Am. Soc. Nephrol. 15: 2032-2041), in cultured mesangial cells, the in vivo status concerning the MAPK1-dependent expression of TGF-β1 has been unknown to date. In this study, MAPK1 was shown to play roles as a regulatory factor upstream of TGF-β1 in glomeruli and subsequently as a modulator in glomerulosclerosis via the expression of ECM components and PAI-1.

In conclusion, the present inventors succeeded in siRNA-mediated intraglomerular gene silencing using a PEG-PLL-based nanocarrier. This system can be utilized not only as a tool for studying the molecular mechanisms for glomerular diseases, but also as a novel strategy for controlling chronic renal diseases or glomerular diseases in the future.

INDUSTRIAL APPLICABILITY

According to the present invention, a novel dosage form for double-stranded ribonucleic acids can be provided, enabling their efficient delivery to target tissue or cells. This leads to expectations for advances in research and treatment of diseases by gene silencing not only in the field of basic research, but also in the medical practice field.

This application is based on a patent application No. 2009-085176 filed in Japan (filing date: Mar. 31, 2009), the contents of which are incorporated in full herein.

The invention claimed is:

1. A polyion complex consisting of a double-stranded ribonucleic acid and a block copolymer of formula (I) or (II), which are electrostatically bound together,
wherein the polyion complex has an average particle diameter of less than 50 nm as measured by a dynamic light scattering measuring method, and
wherein the block copolymer and the double-stranded ribonucleic acid are present in a ratio of N/P=1.2 to 1.5, wherein N represents the total number of cations in the block copolymer, and P represents the total number of phosphoester bonds or equivalent bonds in the double-stranded ribonucleic acid:

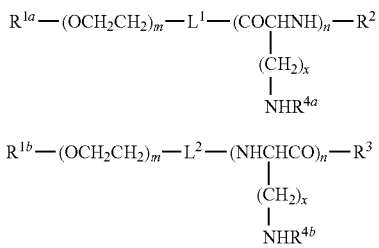

wherein
each of $R^{1a}$ and $R^{1b}$ independently represents a hydrogen atom or an unsubstituted or substituted linear or branched $C_{1-12}$ alkyl group,
each of $L^1$ and $L^2$ represents a linkage group,
$R^2$ represents a hydrogen atom, a protecting group, a hydrophobic group or a polymerizing group,
$R^3$ represents a hydroxyl group, an oxybenzyl group, an —NH—$(CH_2)_a$—X group (X is an amine compound residue comprising one kind or two kinds or more of a primary, secondary or tertiary amine or a quaternary ammonium salt, or a non-amine compound residue; a is an integer of 1 to 5) or an initiator residue,
each of $R^{4a}$ and $^{4b}$ independently represents a hydrogen atom, a protecting group for amino group or —C(=NH)$NHR^5$ ($R^5$ represents a hydrogen atom or a protecting group for an amino group),
m represents an integer of 5 to 20000, n represents an integer of 2 to 5000, and x represents an integer of 1 to 5.

2. The polyion complex according to claim 1, wherein the double-stranded ribonucleic acid is a siRNA.

3. The polyion complex according to claim 1, which has an average particle diameter of 10 to less than 20 nm.

4. A pharmaceutical composition comprising the polyion complex according to claim 1 and a pharmaceutically acceptable carrier.

5. A method comprising delivering the pharmaceutical composition according to claim 4 to a glomerulus or a mesangial cell.

6. The pharmaceutical composition according to claim 5, which is to be used to treat or prevent renal diseases whose pathologic condition occurs mainly in mesangium.

7. A kit for preparing a polyion complex nanocarrier having an average particle diameter of less than 50 nm for delivering a double-stranded ribonucleic acid, comprising
(a) a block copolymer of formula (I) or (II):

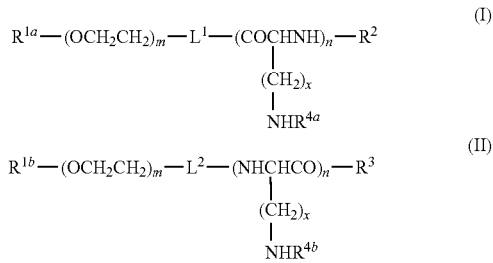

wherein
each of $R^{1a}$ and $R^{1b}$ independently represents a hydrogen atom or an unsubstituted or substituted linear or branched $C_{1-12}$ alkyl group,
each of $L^1$ and $L^2$ represents a linkage group,
$R^2$ represents a hydrogen atom, a protecting group, a hydrophobic group or a polymerizing group,
$R^3$ represents a hydroxy group, an oxybenzyl group, an —NH—$(CH_2)_a$—X group (X is an amine compound residue comprising one kind or two kinds or more of a primary, secondary or tertiary amine or a quaternary ammonium salt, or a non-amine compound residue; a is an integer of 1 to 5) or an initiator residue,
each of $R^{4a}$ and $R^{4b}$ independently represents a hydrogen atom, a protecting group for amino group or —C(=NH)$NHR^5$ ($R^5$ represents a hydrogen atom or a protecting group for an amino group),
m represents an integer of 5 to 20000, n represents an integer of 2 to 5000, and x represents an integer of 1 to 5,
(b) a reagent for dissolving the block polymer and/or double-stranded ribonucleic acid, wherein the block copolymer and reagent are housed in separate containers, and
(c) an instruction sheet stating that the block copolymer and the double-stranded ribonucleic acid be mixed in a ratio of N/P=1.2 to 1.5, wherein N represents the total number of cations in the block copolymer, and P represents the total number of phosphoester bonds or equivalent bonds in the double-stranded ribonucleic acid.

8. The kit according to claim 7, which further comprises a container housing a double-stranded ribonucleic acid.

9. The kit according to claim 7, wherein the instruction sheet states that the kit is to be used for delivery to glomeruli or mesangial cells.

10. A method for treating or preventing a renal disease comprising a step of administering the pharmaceutical composition according to claim 4 to a subject in need thereof.

11. The method according to claim 10, wherein the renal disease is a renal disease pathologically characterized mainly by mesangium.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Combined DNA/RNA Sequence
<220> FEATURE:
<223> OTHER INFORMATION: Synthetic siRNA forward

<400> SEQUENCE: 1
ugcugacucc aaagcucugt t                                              21

<210> SEQ ID NO 2
<211> LENGTH: 21
<212> TYPE: DNA
<213> ORGANISM: Artificial Sequence
<220> FEATURE:
<223> OTHER INFORMATION: Combined DNA/RNA Sequence
<220> FEATURE:
<223> OTHER INFORMATION: Synthetic siRNA reverse

<400> SEQUENCE: 2
ttacgacuga gguuucgaga c                                              21

<210> SEQ ID NO 3
<211> LENGTH: 21
<212> TYPE: DNA
<213> ORGANISM: Artificial Sequence
<220> FEATURE:
<223> OTHER INFORMATION: Combined DNA/RNA Sequence
<220> FEATURE:
<223> OTHER INFORMATION: Synthetic siRNA forward

<400> SEQUENCE: 3
uucuccgaac gugucacgut t                                              21

<210> SEQ ID NO 4
<211> LENGTH: 21
<212> TYPE: DNA
<213> ORGANISM: Artificial Sequence
<220> FEATURE:
<223> OTHER INFORMATION: Combined DNA/RNA Sequence
<220> FEATURE:
<223> OTHER INFORMATION: Synthetic siRNA reverse

<400> SEQUENCE: 4
ttaagaggcu ugcacagugc a                                              21